(12) United States Patent
Belardinelli et al.

(10) Patent No.: US 9,549,926 B2
(45) Date of Patent: Jan. 24, 2017

(54) COMPOSITIONS AND METHODS OF TREATING PULMONARY HYPERTENSION

(71) Applicant: Gilead Sciences, Inc., Foster City, CA (US)

(72) Inventors: Luiz Belardinelli, Palo Alto, CA (US); Hunter Campbell Gillies, El Granada, CA (US); Faquan Liang, San Francisco, CA (US); John Shryock, East Palo Alto, CA (US); Suya Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/079,548

(22) Filed: Nov. 13, 2013

(65) Prior Publication Data

US 2014/0275098 A1 Sep. 18, 2014

Related U.S. Application Data

(63) Continuation of application No. 13/274,013, filed on Oct. 14, 2011, now abandoned.

(60) Provisional application No. 61/497,475, filed on Jun. 15, 2011, provisional application No. 61/490,454, filed on May 26, 2011, provisional application No. 61/393,529, filed on Oct. 15, 2010.

(51) Int. Cl.

| | | |
|---|---|---|
| *A61K 31/505* | (2006.01) | |
| *A61K 31/422* | (2006.01) | |
| *A61K 31/4985* | (2006.01) | |
| *A61K 31/519* | (2006.01) | |
| *A61K 31/53* | (2006.01) | |
| *A61K 45/06* | (2006.01) | |

(52) U.S. Cl.
CPC .......... *A61K 31/505* (2013.01); *A61K 31/422* (2013.01); *A61K 31/4985* (2013.01); *A61K 31/519* (2013.01); *A61K 31/53* (2013.01); *A61K 45/06* (2013.01)

(58) Field of Classification Search
CPC .................................................. G01N 2800/12
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,902,514 A | 2/1990 | Barclay et al. | |
| 5,250,534 A | 10/1993 | Bell et al. | |
| 5,616,345 A | 4/1997 | Geoghegan et al. | |
| 5,703,017 A | 12/1997 | Baumann et al. | |
| 5,859,006 A | 1/1999 | Daugan | |
| 5,932,730 A | 8/1999 | Riechers et al. | |
| 6,362,178 B1 | 3/2002 | Niewöhner et al. | |
| 6,821,975 B1 | 11/2004 | Anderson et al. | |
| 7,109,205 B2 | 9/2006 | Riechers et al. | |
| 7,601,730 B2 | 10/2009 | Riechers et al. | |
| 7,696,206 B2 | 4/2010 | Niewöhner et al. | |
| 7,902,195 B2 | 3/2011 | Hughes | |
| 8,377,933 B2* | 2/2013 | Gerber et al. | 514/243 |
| 2006/0205733 A1* | 9/2006 | Dixon et al. | 514/252.16 |
| 2008/0139593 A1* | 6/2008 | Gerber et al. | 514/274 |
| 2010/0152217 A1 | 6/2010 | Gerber | |
| 2010/0204163 A1 | 8/2010 | Melvin, Jr. et al. | |

FOREIGN PATENT DOCUMENTS

| | | |
|---|---|---|
| CN | 101072564 A | 11/2007 |
| EP | 2101777 | 9/2009 |
| WO | WO-2006/007213 | 1/2006 |
| WO | WO2006/026395 A1 | 3/2006 |
| WO | WO 2008/073927 | 6/2008 |
| WO | WO-2010/062640 | 6/2010 |

OTHER PUBLICATIONS

Spence et al (No Clinically Relevant Pharmacokinetic and Safety Interactions of Ambrisentan in Combination with Tadalafil in Healthy Volunteers, online May 19, 2009, Journal of Pharmaceutical Sciences, vol. 98, pp. 4962-4974).*
Galie et al (Tadalafil Therapy for Pulmonary Arterial Hypertension, May 26, 2009, Circulation, vol. 119, pp. 2894-2903).*
English Translation of Office Action in Korean Patent Application No. 10-2013-7012382 dated Sep. 23, 2014 (6 pages).
English Transtation of Office Action in Japanese Application No. 2013-534043 dated Jul. 24, 2014 (3 pages).
Barst, R.J. et al. "Sitaxsentan Therapy for Pulmonary Arterial Hypertension," *American Journal of Respiratory Critical Care Medicine*, vol. 169, No. 4, pp. 441-447 (2004).
Galie et al., "Tadalafil Therapy for Pulmonary Arterial Hypertension," *Circulation*, vol. 119, pp. 2894-2903 (May 26, 2009).
Iheagwara et al., "Pharmacologic Treatment of Pulmonary Hypertension," *Practica Farmaceutica*, vol. 3, Nr. 1-2, p. 50-56, p. 55, col. 1 to col. 2 (2010).
Kouvelas, D. et al. "PDE5 Inhibitors: In Vitro and In Vivo Pharmacological Profile," *Curr. Pharm. Des.*, vol. 15, No. 30, pp. 3464-3475 (2009).
Limin, M. et al., "Avanafil, A New Rapid-Onset Phosphodiesterase 5 Inhibitor for the Treatment of Erectile Dysfunction," *Expert Opin. Investig. Drugs*, vol. 19, No. 11, pp. 1427-1437 (2010).
Paick, J.S. et al., "Efficacy and Safety of Mirodenafil, a New Oral Phosphodiesterase Type 5 Inhibitor, for Treatment of Erectile Dysfunction," *The Journal of Sexual Medicine*, vol. 5, No. 11, pp. 2672-2680 (2008).
Remington's Pharmaceutical Sciences, 17th Edition, p. 1418 (1985).
Rubin, "Diagnosis and Management of Pulmonary Arterial Hypertension: ACCP Evidence-Based Clinical Practice Guidelines," *Chest*, vol. 126, pp. 7S-10S (2004).
Simonneau, "Updated Clinical Classification of Pulmonary Hypertension," *Journal of the American College of Cardiology*, vol. 54, No. 1, pp. S43-S54 (2009).

(Continued)

*Primary Examiner* — Sean Basquill
*Assistant Examiner* — Mark V Stevens
(74) *Attorney, Agent, or Firm* — Francis O. Ginah

(57) ABSTRACT

Provided are formulations comprising therapeutically effective amounts of ambrisentan or a pharmaceutically acceptable salt thereof and tadalafil or a pharmaceutically acceptable salt thereof and methods of treating and/or preventing pulmonary hypertension by administration of the formulations.

6 Claims, 10 Drawing Sheets

(56) References Cited

OTHER PUBLICATIONS

Spence et al., "No Clinically Relevant Pharmacokinetic and Safety Interactions of Ambrisentan in Combination with Tadalafil in Healthy Volunteers," *Journal of Pharmaceutical Sciences*, vol. 98, pp. 4962-4974 (May 19, 2009).
Toque, H.A. et al., "Pharmacological Characterization of a Novel Phosphodiesterase Type 5 (PDE5) Inhibitor Lodenafil Carbonate on Human and Rabbit Corpus Cavernosum," European Journal of Pharmacology, vol. 591, No. 1-3, pp. 189-195 (2008).
International Search Report and Written Opinion, dated Jun. 6, 2012, in related International Patent Application No. PCT/US2011/056404.
U.S. Office Action, dated Nov. 19, 2012, in related U.S. Appl. No. 13/274,013.
U.S. Office Action, dated May 14, 2013, in related U.S. Appl. No. 13/274,013.
Search Report for CN 2011800608793, English translation, 2 pages, May 16, 2014.
"Guidance for Industry—Toxicity Grading Scale for Healthy Adult and Adolescent Volunteers Enrolled in Preventive Vaccine Clinical Trials," FDA, Sep. 2007.
Barst R., "A review of pulmonary arterial hypertension: role of ambriesental," Vascular Health and Risk Management, (2007), 3(1):11-22.
Buckley, M. et al., "Pharmacokinetic evaluation of ambrisentan", Expert Opin. Drug Metab. Toxicol., (2011), 7(3):371-380.
Cartin-Ceba, R. et al.,"Safety and Efficacy of Ambrisentan for the Treatment of Portopulmonary Hypertension", Chest, (2011) (Pre-published on-line Aug. 12, 2010), 139:109-114.
Cavallito, C. er al., "Sites of action of some unsymmetic bis-quarternary hypotensive agents", Arch. Int. Pharmacodyn, (1955), 101(1):38-48.
Cheng, J., "Ambrisentan for the Management of Pulmonary Artieal Hypertension", Clin. Therapeutics, (2008), 30(5): 825-833.
Fabrer, "Managing patients with PAH:What you need to know about Drug Interactions", Sep. 2010.
Frampton, J., "Ambrisentan", Am. J. Cardiovasc. Drugs, (2011), 11(4):215-226.
Gilchrist, "Ambrisentan for the Treatment of Pulmonary Arterial Hypertension", J. Pharm. Technol., (2008), 24:142-148.
Gilead Sciences Inc., "Gilead terminates Phase III clinical trial of amberisentan in patient with idiopathic pulmonary fibrosi", 2010.
Halank, M. et al., "Ambrisentan Improves Exercise Capacity and Symptoms in Patients with Portopulmonary Hypertension", Z. Gastroenterol, (Sep. 2011), 49:1258-1262.
Hartmann, J.C. et al., "Evaluation of the endothelin receptor antagonists ambrisentan, darusentan, bosentan, and sitaxsentan as substrates and inhibitors of hepatobiliary transporters in sandwich-cultured human hepatocytes", Can. J. Physiol. Pharm., (2010), 88(6):682-691.
Ho, P. C. et al., "Endothelin-1 promotes cytoplasmic accumulation of RIP140 through a $ET_A$-PLC$\beta$-PKC$\epsilon$; pathway", Molec. Cell. Endocrinol., (2012), 351:176-183.
Iglarz, M. et al., "Pharmacology of macitentan, an orally active tissue-targeting dual endothelin receptor antagonist", J. Pharmacol. Exp. Ther., (2008), 327(3):736-745.
Kim, "Riociguat: an upcoming therapy in chronic thromboembolic pulmonary hypertension?", Eur. Respir. Rev., (2010), 19: 681-71.
Kingman, M. et al., "Ambrisentan, an endothelin receptor type A-selective endothelin receptor antagonist, for the treatment of pulmonary arterial hypertension", Expert Opin. Pharmacother., (2009), 10(11):1847-1858.
Ma, et al., "Ambrisentan: A novel selective endothelin A receptor antagonist drug for management of pulmonary arterial hypertension", Chinese Journal of New Drugs and Clinical Remedies, (2009), 28(9):641-644.
MacIntyre, I. et al., "Ambrisentan and its role in the management of pulmonary arterial hypertension", Drugs Today, (2008), 44:875-885.
McGoon, et al. (Poster 1061, presented at 9th Int. PH Conference, Jun. 2010).
McGoon, M. et al., "Ambrisentan Therapy in Patients With Pulmonary Arterial Hypertension Who Discontinued Bosentan or Sitaxsentan Due to Liver Function Test Abnormalities", Chest, (2008).
McGoon, M. et al., "Ambrisentan Therapy in Patients With Pulmonary Arterial Hypertension Who Discontinued Bosentan or Sitaxsentan Due to Liver Function Test Abnormalities", Chest, (2009), 135:122-129.
McLaughlin, V. et al., "ACCF/AHA 2009 Expert Consensus Document on Pulmonary Hypertension: A Report of the American College of Cardiology Foundation Task Force on Expert Consensus Documents and the American Heart Association", J. Am. Coll. Cardiol., (2009), 53(17): 1573-1619.
Myogen, Inc. News Release dated May 19, 2005 (http://investor.myogen.com/phoenix.zhtml?c=135160&p=irol-newsArticle&ID=75965 8&highlight=).
Office Action for U.S. Appl. No. 14/109,899 dated Sep. 13, 2014 (15 pages).
Patel et al., "Pulmonary hypertension in idiopathic pulmonary fibrosis", Chest, (2007), 132: 998-1006.
Pfizer News Release dated Dec. 10, 2010, htt12://12fizer.mediaroom.com/index.QhQ?s=5149&item=223871-httQ://Qfizer.mediaroom.com/index.Qho?s=5149&item=22387%0A %09%09%09%09.
Szarfman, A. et al., "Use of Screening Algorithms and Computer Systems to Efficiently Signal Higher-Than-Expected Combinations of Drugs and Events in the US FD A's Spontaneous Reports Database", Drug Safety, (2002), 25(6):381-392.
Valerio, C. et al., "Safety and Efficacy of Ambrisentan in the Treatment of Pulmonary Arterial Hypertension", Clinical Medicine: Therapeutics, (2009), 1:541-556.
Ware, SF-36® Health Survey Update, (2006), httQ://www.sf-36.org/tools/sf36.shtml.
Wenfang, "Pharmacology and Clinical Study of the New Drug Ambrisentan for Treatment of Pulmonary Arterial Hypertension", Chinese Journal of New Drugs, (2008), 17(23):2070-2077.
Annex to EPO Form 2004, Communication pursuant to Rule 71(3) EPC for EP Patent Application 07855065.4, dated Dec. 1, 2014, 122 pages.
ARIES—Ambrisentan in patients with moderate to severe pulmonary arterial hypertension (PAH):http://clinicaltrials. gov/ct2/show/ NCT00091598?cond=%22Hypertension%22&ran k= 72>, (2004).
Beghetti, D.J., "Current treatment options in children with pulmonary arterial hypertension and experiences with oral bosentan" Eur. J. Clinical Investigation, (2006), 36(Suppl. 3):16-24.
Hoeper (2005) "Drug Treatment of Pulmonary Arterial Hypertension" Drugs, 65(10):1337-1354.
Levine, D.J., "Diagnosis and management of pulmonary arterial hypertension: Implications or respiratory care" Respiratory Care; (2006), 51 (4): 368-381.
Lincoln, "Cyclic GMP and Phosphodiesterase 5 Inhibitor Therapies: What's on the Horizon?" Molecular Pharmcology, American Society for Pharmacology and Experimental Therapeutics; (2004), I30(1):11-13.
Mohan, "Importance of screening and early detection of pulmonary hypertension and current treatment options" J. Postgrad, Med., (2005) 51(2):107.
Myogen Inc.: "Ambrisentan phase II results presented at ATS 2004" prnewswire.com, [online] Jan. 27, 2005: http://www.prnewswire.com/cgibin/stories.pl? ACCT= 104&STORY=/www/story/05-24-2004/0002180826&EDATE=>.
Myogen Inc. News Release, Dec. 4, 2003 (http://www.prnewswire.com/cgibin/stories.pl?ACCT=104&STORY=www/story/12-04-2003/002069898&EDATE).
Myogen Inc. News Release, Jan. 8, 2004 (http://investor.myogen.com/phoenix.zhtml?c=135160&p=irol-newsArticle&ID=759080 &highlight).
Myogen Inc. News Release, Feb. 16, 2004 (http://investor.myogen.com/phoenix.zhtml?c=135160&p=irol-newsArticle&ID=759748 &highlight).

(56) References Cited

OTHER PUBLICATIONS

Myogen Inc. News Release, May 24, 2004 (http://investor.myogen.com/phoenix.zhtml?c=135160&p=irol-newsArticle&ID=759469&highlight).
Myogen Inc. News Release, Feb. 10, 2005 (http://investor.myogen.com/phoenix.zhtml?c=135160&p=irol-newsArticle&ID=759971&highlight).
Myogen Inc. News Reiease, May 23, 2005 (http://investor.myogen.com/phoenix.zhtml?c=135160&p=irol-newsArticle&ID=759656&highlight).
Myogen Inc. News Release, Jul. 21, 2005 (http://investor.myogen.com/phoenix.zhtml?c=135160&p=irol-newsArticle&ID=759650&highlight).
Myogen Inc. News Release, Nov. 10, 2005 (http://investor.myogen.com/phoenix.zhtml?c=135160&p=irol-newsArticle&ID=781654&highlight).
Myogen Inc. News Release, Dec. 12, 2005 (http://investor.myogen.com/phoenix.zhtml?c=135160&p=irol-newsArticie&ID=794738&highiight).
Myogen Inc. News Release, Feb. 13, 2006 (http://investor.myogen.com/phoenix.zhtml?c=135160&p=irol-newsArticle&ID=815989&highlight).
Myogen Inc. News Release, Mar. 2, 2006 (http://investor.myogen.com/phoenix.zhtml?c=135160&p=irol-newsArticleID=824548&highlight).
Myogen Inc. News Release, Apr. 10, 2006 (http://investor.myogen.com/phoenix.zhtml?c=135160&p=irol-newsArticle&ID=840536&highlight).
Myogen Inc. News Release, May 3, 2006 (http://investor.myogen.com/phoenix.zhtml?c=135160&p=irol-newsArticle&ID=851641&highlight).
Myogen Inc. News Release, May 8, 2006 (http://investor.myogen.com/phoenix.zhtml?c=135160&p=irol-newsArticle&ID=853198&highlight).
Myogen Inc. News Release, May 24, 2006 (http://investor.myogen.com/phoenix.zhtml?c=135160&p=irol-newsArticle&ID=860158&highlight).
Myogen Jun. 2006 presentation available at library corporate-ir.net/library/13/135/135160/items/203236/Junepresentation.pdf.
Myogen Inc. News Release, Aug. 7, 2006 (http://investor.myogen.com/phoenix.zhtml?c=135160&p=irol-newsArticle&I0=892987&highlight).
Myogen Inc. News Release, Sep. 5, 2006 (http://investor.myogen.com/phoenix.zhtml?c=135160&p=irol-newsArticle&ID=902050&highlight).
Myogen Inc. News Release, Oct. 10, 2006 (http://investor.myogen.com/phoenix.zhtml?c=135160&p=irol-newsArticle&ID=913787&highlight).
International Search Report and Written Opinion in PCT/US2007/087058 dated Apr. 21, 2008, 11 pages.
Patent Examination Report No. 1 for AU Application No. 2011315891 dated Jun. 3, 2014, 2 pages.
Office Action in Canadian Application No. 2814518 dated Feb. 27, 2014, 2 pages.
Office Action in Chinese Application No. 2011800608793 dated May 28, 2014, 9 pages (English translation also provided).
Communication pursuant to Rules 161(2) and 162 EPC in European Application No. 11833507.4 dated Oct. 25, 2013, 2 pages.
Office Action in Korean Application No. 2013-7012382 dated Mar. 20, 2015, 3 pages (English translation also provided).
Examination Report in New Zealand Application No. 707213 dated May 12, 2015, 3 pages.
Office Action on Formalities in Japanese Application No. 2013-534043 dated Feb. 5, 2015, 4 pages (English translation also provided).
Office Action in Eurasian Application No. 201390428/28 Apr. 7, 2015, 2 pages (English translation also provided).
Korean Patent Application No. 10-2013-7012382 Office Action dated Jul. 21, 2015.
Search Report in Taiwan Application 100137481 dated Aug. 10, 2015.
"Ambrisentan (Letairis) for Pulmonary Arterial Hypertension", Medical Letter on Drugs and Therpeutics, New Rochelle, NY, US 49(1272):87-88, 2007.
"Classification of Pulmonary Arterial Hypertension (PAH)", retrieved from the Internet http://www.pah-info.com/classification_of_PH, Dec. 16, 2015, 3 pages.
Cada et al., (2007), "Ambrisentan", Hospital Pharmacy, Lippincott, Philadelphia US, 42(12):1145-1154.
Examiner's Report in Canadian Application No. 2669536 dated Apr. 30, 2015, 3 pages.
Extended European Search Report for EP Application 15168201.0 dated Nov. 9, 2015, 10 pages.
Galie et al. (2005) "Ambrisentan therapy for pulmonary arterial hypertension", J. Am. Coll.; Cardiol. 46(3):529-535.
International Preliminary Report on Patentability in PCT Application No. PCT/US2011/056404 dated Sep. 10, 2013, 6 pages.
International Search Report (ISR) and Written Opinion (WO) in PCT/US2007/087058 dated Apr. 21, 2008, 11 pages.
McLaughlin et al., (2006), "Contemporary Reviews in Cardiovascular Medicine—Pulmonary Arterial Hypertension", Circulation, Lippincott Williams and Wilkins, US, 114(13):1417-1431.
Mealy et al., (2005), " Annual Update 2004/2005—Treatment of Respiratory Disorders", Drugs of the Future, Prous Sciences, ES, 30(1):51-107.
Office Action for U.S. Appl. No. 14/695,775 dated Dec. 7, 2015, 15 pages.
Rosenzweig, (2006), "Emerging Treatments for 1-23 Pulmonary Arterial Hypertension", Expert Opinion on Emerging Drugs, Informa Healthcare UK 11(4):609-619.
Rubin et al., "Ambrisentan for pulmonary arterial hypertension", Future Cardiol. 1(4):1-8, 2005.
European Patent Application No. 07855065.4 Notice of Opposition dated Feb. 25, 2016.
European Patent Application No, 07855065.4 Opponent's Grounds for Opposition (Translation) from Notice of Opposition dated Feb. 25, 2016.
Bharani et al. (2003), The Efficacy and tolerability of Silderiafil in Patients with Moderate-to-Severe Pulmonary Hypertension, *Indian Heart Journal*, vol. 55:55-59.
Dufton et al. (2006) "No Clinically Relevant Pharmacokinetic Interaction Between Ambrisentan and Sildenafil", *Chestnet*, Abstract.
Galie et al. (2005) "Sildenafil Citrate Therapy for Pulmonary Arterial Hypertension" *The New England Journal of Medicine*, vol. 353, No. 20:2148-2157.
McLaughlin et al. (2005), "Pulmonary Arterial Hypertension" *American Journal of Respiratory and Critical Care Medicine*, vol. 171:1199-1200.
Myogen Inc. (2002) "Abstract Ambristentan" *Pubmed—indexed for Medline*.
Paul et al. (2005) "Bosentan Decreases the Plasma Concentration of Sildenafil When Coprescribed in Pulmonary Hypertension" *British Journal of Clinical Pharmacology*, vol. 60, No. 1:107-112.
Wilkins et al. (2005) "Sildenafil versus Endothelin Receptor Antagonist for Pulmonary Hypertension (SERAPH) Study" *American Journal of Respiratory and Critical Care Medicine*, vol. 171:1292-1297.
McLaughlin et al. (2009) "Pulmonary Arterial Hypertension: The Most Devastating Vascular Complication of Systemic Sclerosis", *Rheumatology* (Oxford, England) vol. 48(3), ISSN 1462-1332: iii25-iii31, DOI: http://dx.doi.ort/10.1093/rhematology/kep107.
Office Action (translation) dated Mar. 14, 2016 for Mexican Application No. MX/a/2013/004190.

\* cited by examiner

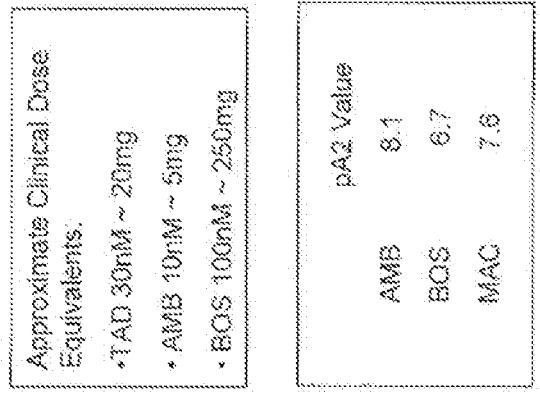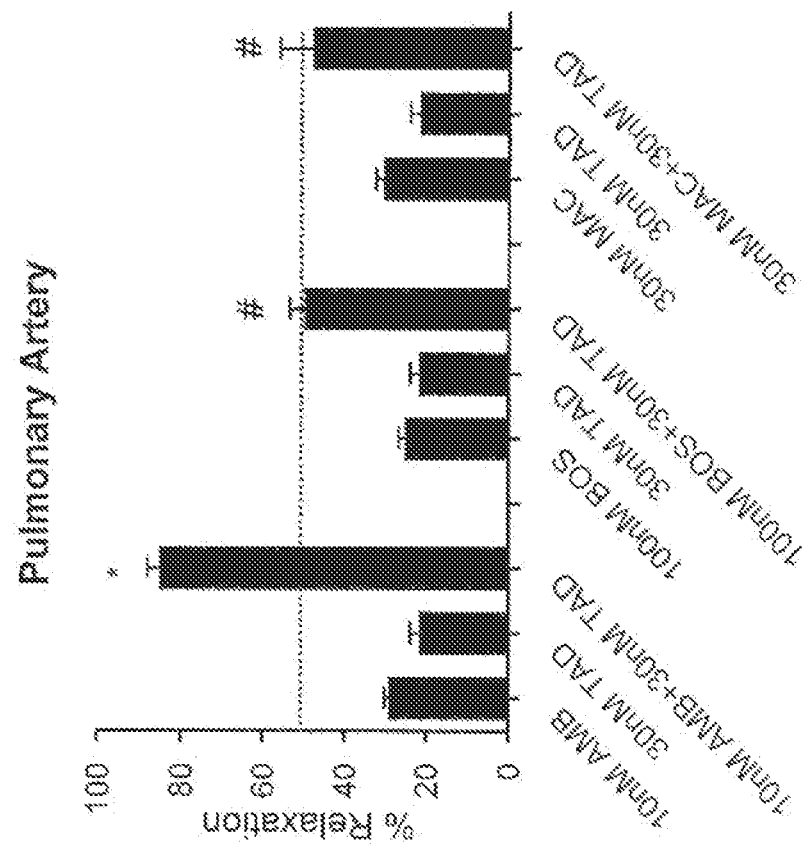
FIG. 2

COMPOSITIONS AND METHODS OF TREATING PULMONARY HYPERTENSION

CROSS-REFERENCE TO RELATED APPLICATION

This application is a continuation of U.S. application Ser. No. 13/274,013, filed Oct. 14, 2011, which claims the benefit under 35 U.S.C. §119(e) of U.S. Provisional Application No. 61/393,529 filed Oct. 15, 2010, U.S. Provisional Application No. 61/490,454 filed May 26, 2011, and U.S. Provisional Application No. 61/497,475 filed Jun. 15, 2011. The entire disclosure of the applications identified in this paragraph is incorporated herein by reference.

FIELD

The present disclosure relates to methods of treating and/or preventing pulmonary hypertension by administration of therapeutically effective amounts of a selective type-A endothelin receptor antagonist and a phosphodiesterase type 5 inhibitor. This disclosure also relates to pharmaceutical formulations that are suitable for such administration.

BACKGROUND

Pulmonary hypertension (PH) has been previously classified as primary (idiopathic) or secondary. Recently, the World Health Organization (WHO) has classified pulmonary hypertension into five groups:

Group 1: pulmonary arterial hypertension (PAH);
Group 2: PH with left heart disease;
Group 3: PH with lung disease and/or hypoxemia;
Group 4: PH due to chronic thrombotic and/or embolic disease; and
Group 5: miscellaneous conditions (e.g., sarcoidosis, histiocytosis X, lymphangiomatosis and compression of pulmonary vessels).
See, for example, Rubin (2004) Chest 126:7-10.

Pulmonary arterial hypertension (PAH) is a particular type of PH and is a serious, progressive and life-threatening disease of the pulmonary vasculature, characterized by profound vasoconstriction and an abnormal proliferation of smooth muscle cells in the walls of the pulmonary arteries. Severe constriction of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in pulmonary vascular resistance (PVR) and sustained elevations in pulmonary artery pressure (PAP), which ultimately lead to right ventricular failure and death. Patients diagnosed with PAH have a poor prognosis and equally compromised quality of life, with a mean life expectancy of 2 to 5 years from the time of diagnosis if untreated.

Endothelin-1 (ET-1) is the primary member of a family of potent vasoconstrictor peptides, which are known to play an essential role in mammalian cardiovascular physiology. ET-1 is synthesized de novo and released from endothelial cells in response to a variety of factors, including angiotensin II, catecholamines, cytokines, hypoxia and shear stress. Two receptor subtypes, endothelin receptor type A ($ET_A$) and endothelin receptor type B ($ET_B$), mediate the effects of ET-1. In humans, the $ET_A$ receptor is preferentially expressed in vascular smooth muscle cells and is primarily responsible for the vasoconstrictive effects of ET-1. In contrast, $ET_B$ receptors are found mainly in the vascular endothelium, and their activation results in vasodilatation via production of nitric oxide and prostacyclin. The $ET_B$ receptor is also involved in regulation of circulating concentrations of ET-1, through effects on endothelin converting enzyme (ECE-1) expression, and the synthesis and reuptake of ET-1 by endothelial cells.

Ambrisentan is a non-sulfonamide, propanoic acid-class endothelin receptor antagonist (ERA) with high affinity (~12 pM) for the $ET_A$ receptor. Ambrisentan is approved for sale by the U.S. Food and Drug Administration (FDA) for once-daily treatment of PAH and is marketed under the trade name Letairis®. Other selective type-A receptor antagonists include sitaxentan, atrasentan, and BQ-123.

Additional drugs such as phosphodiesterase type 5 inhibitors (PDE5 inhibitor) are also approved for use in treating PAH. PDE5 inhibitors are drugs used to block the degradative action of phosphodiesterase type 5 on cyclic GMP in the arterial wall smooth muscle within the lungs and in the smooth muscle cells lining the blood vessels supplying the corpus cavernosum of the penis.

Tadalafil is a PDE5 inhibitor, currently marketed under the name Adcirca® for the treatment of pulmonary arterial hypertension. The approved dose for pulmonary arterial hypertension is 40 mg (two 20-mg tablets) once daily. Adverse effects of tadalafil include hypotension, vision loss, hearing loss and priapism. Thus, methods of increasing the anti-PH efficacy of selective type-A ERA and PDE5 inhibitors, as well as reducing the potential adverse effects, are highly desirable. Other PDE5 inhibitors on the market or during development include avanafil, lodenafil, mirodenafil, sildenafil citrate, vardenafil and udenafil.

U.S. Patent Publication No. 2008/0139593 describes a method for treating pulmonary hypertension, comprising administration of a therapeutically effective amount of ambrisentan to a patient, wherein, at baseline, time from the first diagnosis of the condition in the subject is not greater than about two years. Also described is ambrisentan in combination with one or more suitable drugs selected from prostanoids, PDE5 inhibitors such as sildenafil, tadalafil, and vardenafil, ERAs, calcium channel blockers, arylalkylamines, dihydropyridine derivatives, piperazine derivatives and other suitable compounds for use in combination therapy.

It has now been discovered that the combination of a selective type-A ERA and a PDE5 inhibitor has beneficial co-action resulting in potent relaxation of pulmonary contractions. For example, the co-action of ambrisentan and tadalafil provides enhanced efficacy in reducing endothelin-induced contraction of rat pulmonary arteries and aortas.

SUMMARY OF THE DISCLOSURE

This disclosure describes the administration of a selective type-A endothelin receptor antagonist (selective type-A ERA) in combination with a phosphodiesterase type 5 inhibitor (PDE5 inhibitor) which co-acts in relaxating pulmonary contractions and/or inhibiting hypoxia-induced pulmonary arterial pressure (PAP). The ability to relax pulmonary contraction or inhibit PAP is useful for treating and preventing pulmonary hypertension in patients, as well as a variety of other conditions, which are described herein. This combination therapy leads to enhanced therapeutic effects when the selective type-A ERA is administered in a therapeutically effective dose and the PDE5 inhibitor is administered in a therapeutically effective dose. Either one or both of the selective type-A ERA and the PDE5 inhibitor may be administered in an amount less than their respective standard therapeutic doses due to their co-action.

Certain ratios of the two agents even increase effectiveness of the co-action so that it is substantially greater than the sum of effectiveness of mono-administration of each agent (i.e. administration of a single agent). In one aspect, the ratio of the amount of the selective type-A ERA and the amount of the PDE5 inhibitor, in order to get such enhanced effectiveness, can be from about 2:1 to about 1:3. Alternatively, the ratio of the amount of the selective type-A ERA and the amount of the PDE5 inhibitor can range from 1:1, 1:1.5, 1:2, 1:2.5, 1:3, 1:4, 1:5, 1:6, 1:7, 1:8, 1:9 or 1:10 to about 1:4, 1:5, 1:6, 1:7, 1:8, 1:9, 1:10, 1:11, 1:12, 1:15 or 1:20. In another aspect, such combinations can achieve an effectiveness that is at least about 5%, or alternatively 10%, 15%, 20%, 25%, 30%, 35%, 40%, 45%, 50%, 55%, 60%, 65%, 70%, 80%, 90% or 100% greater than the sum of effectiveness of mono-administration of each agent.

Non-limiting examples of selective type-A ERA include ambrisentan and sitaxentan and pharmaceutically acceptable salts thereof. In one aspect, the selective type-A ERA is ambrisentan. Examples of PDE5 inhibitors include: without limitation, tadalafil, avanafil, lodenafil, mirodenafil, sildenafil citrate, vardenafil and udenafil and pharmaceutically acceptable salts thereof. In one aspect, the PDE5 inhibitor is tadalafil.

Accordingly, in one aspect, this disclosure is directed to a method for treatment and/or prevention of pulmonary hypertension in a patient in need thereof. The method comprises administration of a therapeutic amount of ambrisentan or a salt thereof in combination with tadalafil or a salt thereof, wherein the ratio of the amount of ambrisentan or a salt thereof and the amount of tadalafil or a salt thereof is in a range from about 1:1 to about 1:10, or alternatively from about 1:2 to about 1:5, or alternatively about 1:3.

Another aspect of this disclosure provides a method for treating or preventing pulmonary hypertension in a patient in need thereof comprising administering to the patient therapeutic amounts of ambrisentan or a salt thereof in combination with tadalafil or a salt thereof, wherein the effectiveness of administration of the ambrisentan and the tadalafil is at least about 25%, or alternatively 40% or 50%, greater than the sum of effectiveness of mono-administrations of the ambrisentan and the tadalafil.

Further provided, in one aspect, is a method for treating or preventing pulmonary hypertension in a patient in need thereof comprising administering to the patient, once daily, therapeutic amounts of ambrisentan or a salt thereof in combination with tadalafil or a salt thereof, wherein the ratio of the amount of ambrisentan or a salt thereof and the amount of tadalafil or a salt thereof is about 1:3.

In any of the embodiments described herein, the pulmonary hypertension comprises pulmonary arterial hypertension (PAH), including but not limited to idiopathic PAH, familial PAH or PAH associated with another disease or condition. In one aspect, the PAH at baseline is of WHO Class I, II, III or IV.

In another aspect, provided is a method for inhibiting endothelin-induced vasoconstriction in a patient in need thereof comprising administering to the patient therapeutic amounts of ambrisentan or a salt thereof in combination with tadalafil or a salt thereof, wherein (a) the ratio of the amount of ambrisentan or a salt thereof and the amount of tadalafil or a salt thereof is in a range from about 1:1 to about 1:10 and/or (b) the effectiveness of administration of the ambrisentan and the tadalafil is at least about 25% greater than the sum of effectiveness of mono-administrations of the ambrisentan and the tadalafil.

Also provided, in one aspect, is a method for treating or preventing a disease in a patient in need thereof comprising administering to the patient therapeutic amounts of ambrisentan or a salt thereof in combination with tadalafil or a salt thereof, wherein the disease is selected from the group consisting of hypertension, pulmonary hypertension, myocardial infarction, angina pectoris, acute kidney failure, renal insufficiency, cerebral vasospasms, cerebral ischemia, subarachnoid hemorrhages, asthma, atherosclerosis, intravascular coagulation, restenosis after angioplasty, hypertension caused by ischemia or intoxication, kidney failure caused by ischemia or intoxication, Raynaud's syndrome and asthmatic airway condition, and wherein (a) the ratio of the amount of ambrisentan or a salt thereof and the amount of tadalafil or a salt thereof is in a range from about 1:1 to about 1:10 and/or (b) the effectiveness of administration of the ambrisentan and the tadalafil is at least about 25% greater than the sum of effectiveness of mono-administrations of the ambrisentan and the tadalafil.

Still further provided is a method for reducing undesirable side effects of ambrisentan or a salt thereof comprising administering to the patient a therapeutic amount of tadalafil or a salt thereof, wherein (a) the ratio of the amount of ambrisentan or a salt thereof and the amount of tadalafil or a salt thereof is in a range from about 1:1 to about 1:10 and/or (b) the effectiveness of administration of the ambrisentan and the tadalafil is at least about 25% greater than the sum of effectiveness of mono-administrations of the ambrisentan and the tadalafil.

A method for reducing a therapeutically effective dose of ambrisentan or a salt thereof is also provided, the method comprising administering to the patient a therapeutic amount of tadalafil or a salt thereof, wherein (a) the ratio of the amount of ambrisentan or a salt thereof and the amount of tadalafil or a salt thereof is in a range from about 1:1 to about 1:10 and/or (b) the effectiveness of administration of the ambrisentan and the tadalafil is at least about 25% greater than the sum of effectiveness of mono-administrations of the ambrisentan and the tadalafil.

Yet in one aspect, this disclosure provides a method for reducing undesirable side effects of tadalafil or a salt thereof comprising administering to the patient a therapeutic amount of ambrisentan or a salt thereof, wherein (a) the ratio of the amount of ambrisentan or a salt thereof and the amount of tadalafil or a salt thereof is in a range from about 1:1 to about 1:10 and/or (b) the effectiveness of administration of the ambrisentan and the tadalafil is at least about 25% greater than the sum of effectiveness of mono-administrations of the ambrisentan and the tadalafil.

In another aspect, provided is a method for reducing a therapeutically effective dose of tadalafil or a salt thereof comprising administering to the patient a therapeutic amount of ambrisentan or a salt thereof, wherein (a) the ratio of the amount of ambrisentan or a salt thereof and the amount of tadalafil or a salt thereof is in a range from about 1:1 to about 1:10 and/or (b) the effectiveness of administration of the ambrisentan and the tadalafil is at least about 25% greater than the sum of effectiveness of mono-administrations of the ambrisentan and the tadalafil.

Pharmaceutical formulations are also provided. One aspect provides a pharmaceutical formulation comprising therapeutic amounts of tadalafil or a salt thereof and ambrisentan or a salt thereof, and a pharmaceutically acceptable carrier, wherein (a) the ratio of the amount of ambrisentan or a salt thereof and the amount of tadalafil or a salt thereof is in a range from about 1:1 to about 1:10 and/or (b) the effectiveness of combination of the ambrisentan and the tadalafil is at least about 25% greater than the sum of effectiveness of mono-administrations of the ambrisentan and the tadalafil.

In one aspect, this disclosure provides a method for treating pulmonary hypertension in a patient comprising administering a therapeutically effective amount of a combination therapy comprising of a selective type-A endothelin receptor antagonist, in combination with a PDE5 inhibitor and metabolites thereof, co-acting to provide therapeutic benefit to patients with pulmonary hypertension in absence of a substantial deleterious side effect in a therapeutically effective ratio in a range from about 1:1 to about 1:10.

In another aspect, this invention discloses a method for treating pulmonary hypertension in a patient comprising administering a therapeutically effective amount of a combination therapy comprising of a selective type-A endothelin receptor antagonist, a PDE5 inhibitor, and a third active agent effective for the treatment of pulmonary hypertension or a related condition, and metabolites thereof, co-acting to provide therapeutic benefit to patients with pulmonary hypertension in absence of a substantial deleterious side effect in a therapeutically effective molar ratio in a range from about 1:1 to about 1:10.

In one aspect, this disclosure provides a pharmaceutical formulation of a combination therapy comprising therapeutic amounts of a selective type-A endothelin receptor antagonist and a PDE5 inhibitor co-acting to provide therapeutic benefit to patients with pulmonary hypertension in absence of a substantial deleterious side effect in a therapeutically effective ratio in a range from about 1:1 to about 1:10.

In one aspect, this disclosure provides a pharmaceutical formulation comprising therapeutic amounts of tadalafil or a salt thereof and ambrisentan or a salt thereof, and a pharmaceutically acceptable carrier, wherein the ratio of the amount of ambrisentan or a salt thereof and the amount of tadalafil or a salt thereof is about 1:3.

In another aspect, this disclosure provides a pharmaceutical formulation of a combination therapy comprising a selective type-A endothelin receptor antagonist, a PDE5 inhibitor, and a third active agent effective for the treatment of pulmonary hypertension or a related condition, and metabolites thereof, co-acting to provide therapeutic benefit to patients with pulmonary hypertension in absence of a substantial deleterious side effect in a therapeutically effective molar ratio in a range from about 1:1 to about 1:10.

BRIEF DESCRIPTION OF THE DRAWINGS

As used throughout the Figures, the term "AMB" refers to ambrisentan, "TAD" refers to tadalafil, "BOS" refers to bosentan, and "MAC" refers to macitentan.

FIG. 2 shows that the combination of ambrisentan and tadalafil exhibited more than additive effects than monotherapy of either drug, and thus, beneficial co-action exists between ambrisentan and tadalafil. Such co-action, however, was not observed between non-selective ERA, such as bosentan and macitentan, when administered with tadalafil. *$p<0.01$ vs. Ambrisentan (AMB) or Tadalafil (TAD). #$p<0.05$ vs. mono-administrations of Bosentan (BOS), Macitentan (MAC) and TAD or combination of ABM with TAD. ---: represents the predicted additive effect of AMB with TAD.

DETAILED DESCRIPTION OF THE DISCLOSURE

1. Definitions and General Parameters

Figure 1:
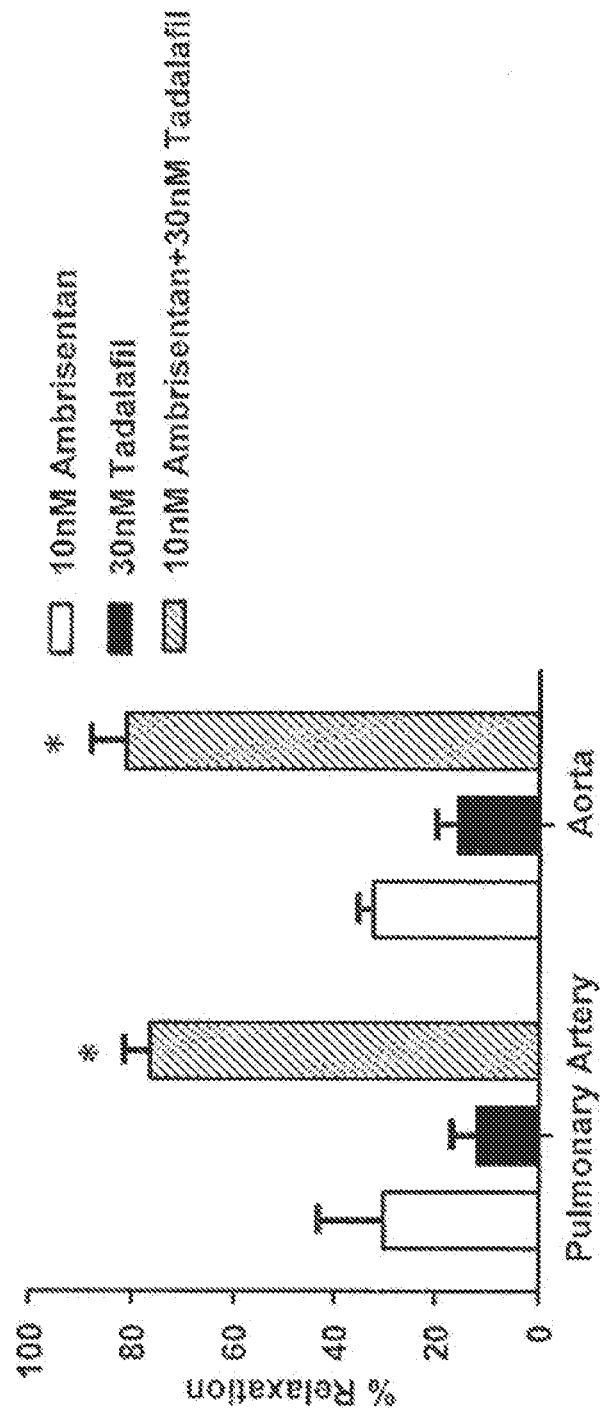
FIG. 1 shows that ambrisentan (10 nM) and tadalafil (30 nM), in combination, relaxed endothelin-induced contraction of rat pulmonary arteries and aortas significantly more effectively than mono-administration of either drug. Data are expressed as mean±SEM, n=3. *$p<0.01$ vs. monotherapy of 10 nM Ambrisentan or 30 nM tadalafil.

As used in the present specification, the following words and phrases are generally intended to have the meanings as set forth below, except to the extent that the context in which they are used indicates otherwise.

It is to be noted that as used herein and in the claims, the singular forms "a," "an" and "the" include plural referents unless the context clearly dictates otherwise. Thus, for example, reference to "a pharmaceutically acceptable carrier" in a composition includes two or more pharmaceutically acceptable carriers, and so forth.

"Comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

An "endothelin receptor antagonist (ERA)" is an agent that blocks endothelin receptors. There are at least two major known endothelin receptors, $ET_A$ and $ET_B$, both of which are G protein-coupled receptors whose activation result in elevation of intracellular-free calcium. Three main kinds of ERAs exist: selective type-A receptor antagonists, e.g., sitaxentan, ambrisentan, atrasentan, BQ-123, which affect endothelin A receptors; dual antagonists, e.g., bosentan, macitentan, tezosentan, which affect both endothelin A and B receptors; and selective type-B receptor antagonists, e.g., BQ-788, which affect endothelin B receptors.

A "selective type-A endothelin receptor antagonist" or "selective type-A ERA" selectively targets the type-A endothelin receptor.

"Ambrisentan" or "AMB" is described in U.S. Pat. Nos: 5,703,017; 5,932,730 and 7,109,205. It refers to the chemical compound, (2S)-2-[(4,6-dimethylpyrimidin-2-yl)oxy]-3-methoxy-3,3-diphenylpropanoic acid and has the following chemical formula:

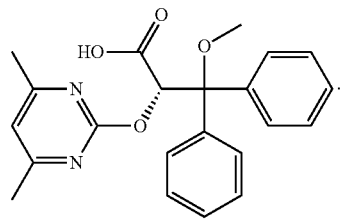 [SMILES: COC(c1ccccc1)(c1ccccc1)[C@H](Oc1nc(C)cc(C)n1)C(=O)O]

Ambrisentan is approved for sale by the U.S. Food and Drug Administration (FDA) for once-daily treatment of PAH and is marketed under the trade name Letairis®. In Europe, Ambrisentan is approved under the trade name Volibris®.

"Ambrisentan" as used herein is intended to include the metabolites of ambrisentan described in U.S. Patent Publication No. 2010/0204163. The ambrisentan metabolites include the compounds having the following chemical formula:

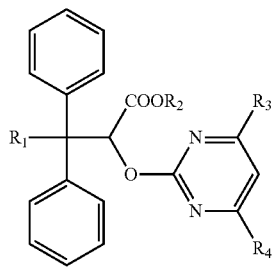
(I)

wherein $R^1$ is —OH or —OCH$_3$; $R^2$ is —H, lower alkyl or glycosidyl; and $R^3$ and $R^4$ are independently —CH$_3$, —C(O)H or —CH$_2$OR$^6$, wherein $R^6$ is —H or a hydrocarbyl group having 1 to 20 carbon atoms.

"Sitaxentan" refers to the chemical compound N-(4-chloro-3-methyl-1,2-oxazol-5-yl)-2-[(6-methyl-2H-1,3-benzodioxol-5-yl)acetyl]thiophene-3-sulfonamide, and its pharmaceutically acceptable salts. Sitaxentan is described in Barst RJ et al., (2004) *American Journal of Respiratory Critical Care Medicine* 169 (4): 441-7. Sitaxentan has the following chemical formula:

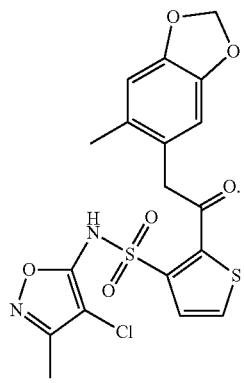 [SMILES: Cc1cc2c(cc1CC(=O)c1sccc1S(=O)(=O)Nc1onc(C)c1Cl)OCO2]

Sitaxentan was marketed as Thelin® for the treatment of PAH in 2008 but was later removed from the market in 2010.

A "phosphodiesterase type 5 inhibitor" or "PDE5 inhibitor" refers to an agent that blocks the degradative action of phosphodiesterase type 5 on cyclic GMP in the arterial wall smooth muscle within the lungs and in the smooth muscle cells lining the blood vessels supplying the corpus cavernosum of the penis. PDE5 inhibitors are used for the treatment of pulmonary hypertension and in the treatment of erectile dysfunction. Examples of PDE5 inhibitors include, without limitation, tadalafil, avanafil, lodenafil, mirodenafil, sildenafil citrate, vardenafil and udenafil and pharmaceutically acceptable salts thereof. In one aspect, the PDE5 inhibitor is tadalafil.

"Tadalafil" or "TAD" is described in U.S. Pat. Nos. 5,859,006 and 6,821,975. It refers to the chemical compound, (6R-trans)-6-(1,3-benzodioxol-5-yl)-2,3,6,7,12,12a-hexahydro-2-methyl-pyrazino [1', 2':1,6] pyrido[3,4-b]indole-1,4-dione and has the following chemical formula:

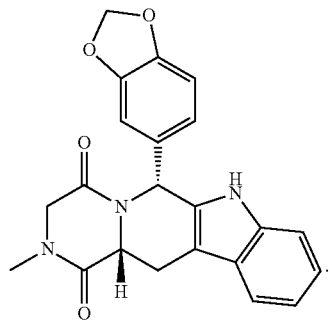 [SMILES: CN1CC(=O)N2[C@H](c3ccc4c(c3)OCO4)c3[nH]c4ccccc4c3C[C@@H]2C1=O]

Tadalafil is currently marketed in pill form for treating erectile dysfunction (ED) under the trade name Cialis® and under the trade name Adcirca® for the treatment of PAH.

"Avanafil" refers to the chemical compound 4-[(3-Chloro-4-methoxybenzyl)amino]-2-[(hydroxymethyl)-1-pyrrolidinyl]-N-(2-pyrimidinylmethyl)-5-pyrimidinecarboxamide, and its pharmaceutically acceptable salts. Avanafil is described in Limin M. et al., (2010) *Expert Opin Investig Drugs*, 19(11):1427-37. Avanafil has the following chemical formula:

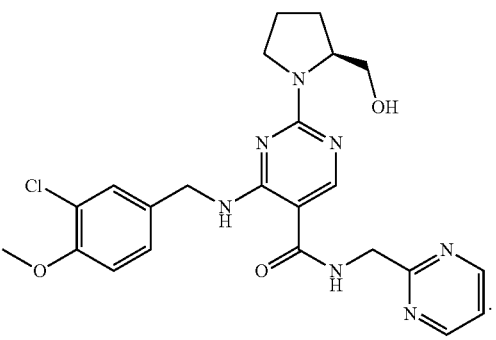 [SMILES: COc1ccc(CNc2nc(N3CCC[C@H]3CO)ncc2C(=O)NCc2ncccn2)cc1Cl]

Avanafil is being developed for erectile dysfunction. Avanafil currently has no trademarked term associated with it but it is being developed by Vivus Inc.

"Lodenafil" refers to the chemical compound, bis-(2-{4-[4-ethoxy-3-(1-methyl-7-oxo-3-propyl-6,7-dihydro-1H-pyrazolo[4,3-d]pyrimidin-5-yl)-benzenesulfonyl]piperazin-1-yl}-ethyl)carbonate and has the following chemical formula:

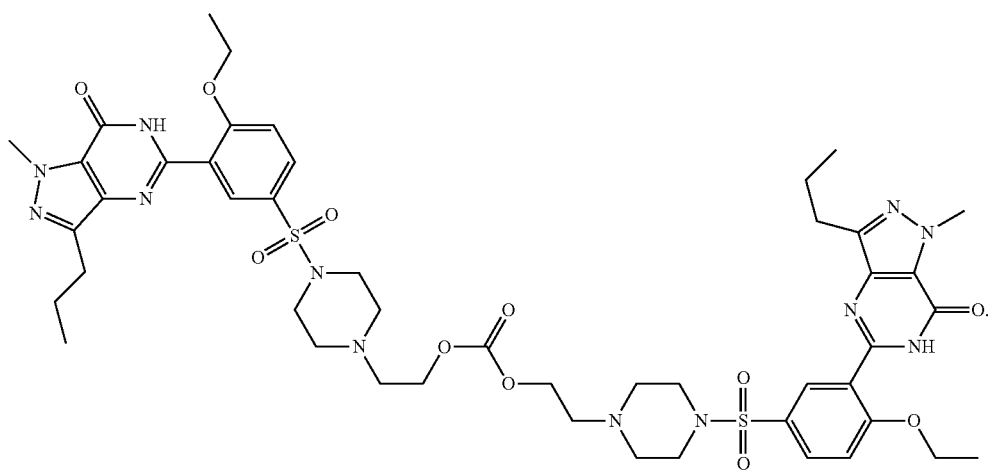 [SMILES: CCCc1nn(C)c2c(=O)[nH]c(-c3cc(S(=O)(=O)N4CCN(CCOC(=O)OCCN5CCN(S(=O)(=O)c6ccc(OCC)c(-c7nc8c(CCC)nn(C)c8c(=O)[nH]7)c6)CC5)CC4)ccc3OCC)nc12]

More information about lodenafil is available at Toque HA et al., (2008) *European Journal of Pharmacology*, 591(1-3):189-95. Lodenafil is manufactured by Cristália Produtos Químicos e Farmacêuticos in Brazil and sold there under the brand-name Helleva®. It has undergone Phase III clinical trials, but is not yet approved for use in the United States by the U.S. FDA.

"Mirodenafil" refers to the chemical compound, 5-Ethyl-3,5-dihydro-2-[5-([4-(2-hydroxyethyl)-1-piperazinyl]sulfonyl)-2-propoxyphenyl]-7-propyl-4H-pyrrolo[3,2-d]pyrimidin-4-one and has the following chemical formula:

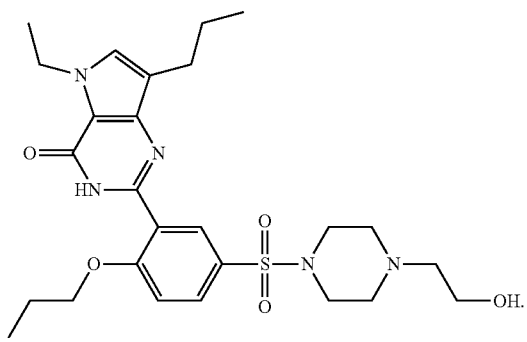 [SMILES: CCCOc1ccc(S(=O)(=O)N2CCN(CCO)CC2)cc1-c1nc2c(CCC)cn(CC)c2c(=O)[nH]1]

More information about mirodenafil can be found at Paick JS et al., (2008) *The Journal of Sexual Medicine*, 5 (11): 2672-80. Mirodenafil is not currently approved for use in the United States but clinical trials are being conducted.

"Sildenafil citrate," marketed under the name Viagraq®, is described in U.S. Pat. No. 5,250,534. It refers to 1-[4-ethoxy-3-(6,7-dihydro-1-methyl-7-oxo-3-propyl-1H-pyrazolo[4,3-d]pyrimidin-5-yl)phenylsulfonyl]-4-methylpiperazine and has the following chemical formula:

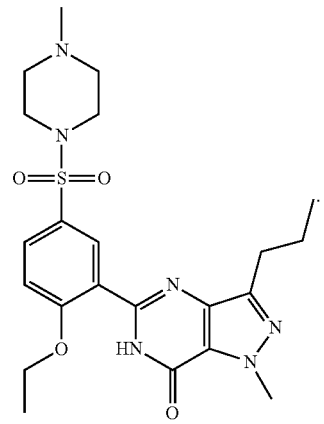 [SMILES: CCCc1nn(C)c2c(=O)[nH]c(-c3cc(S(=O)(=O)N4CCN(C)CC4)ccc3OCC)nc12]

Sildenafil citrate, sold as Viagra®, Revatio® and under various other trade names, is indicated to treat erectile dysfunction and PAH.

"Vardenafil" refers to the chemical compound, 4-[2-Ethoxy-5-(4-ethylpiperazin-1-yl)sulfonyl-phenyl]-9-methyl-7-propyl-3,5,6,8-tetrazabicyclo[4.3.0]nona-3,7,9-trien-2-one and has the following chemical formula:

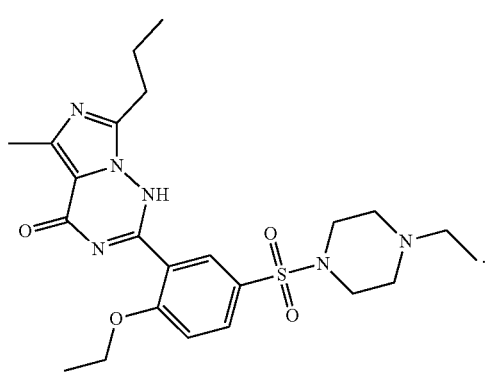 [SMILES: CCCc1nc(C)c2c(=O)nc(-c3cc(S(=O)(=O)N4CCN(CC)CC4)ccc3OCC)[nH]n12]

Vardenafil is described in U.S. Pat. Nos. 6,362,178 and 7,696,206. Vardenafil is marketed under the trade name Levitra® for treating erectile dysfunction.

"Udenafil" refers to the chemical compound, 3-(1-methyl-7-oxo-3-propyl-4,7-dihydro-1H-pyrazolo[4,3-d]pyrimidin- 5-yl)-N-[2-(1-methylpyrrolidin-2-yl)ethyl]-4-propoxyben-zenesulfonamide and has the following chemical formula:

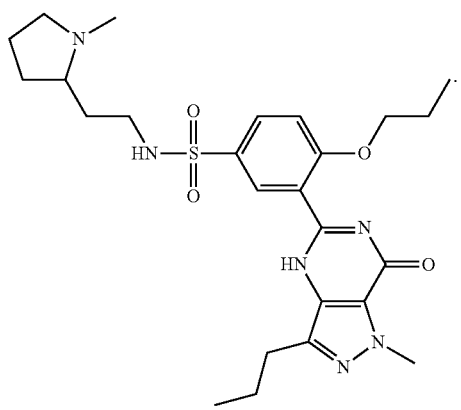 [SMILES: CCCOc1ccc(S(=O)(=O)NCCC2CCCN2C)cc1-c1nc(=O)c2c([nH]1)c(CCC)nn2C]

More information about udenafil can be found at Kouvelas D. et aL, (2009) *Curr Pharm Des*, 15(30):3464-75. Udenafil is marketed under the trade name Zydena® but not approved for use in the United States.

Each of the compounds described above, as used throughout, is intended to include a free acid, free base, or a pharmaceutically acceptable salt thereof.

As used herein, the term "salt" refers to a pharmaceutically acceptable salt of a compound that is derived from a variety of physiologically acceptable organic and inorganic counter ions. Such counter ions are well known in the art and include, by way of example only, sodium, potassium, calcium, magnesium, aluminum, lithium and ammonium, for example tetraalkylammonium, and the like when the molecule contains an acidic functionality; and when the molecule contains a basic functionality, salts of organic or inorganic acids, such as hydrochloride, sulfate, phosphate, diphosphate, nitrate hydrobromide, tartrate, mesylate, acetate, malate, maleate, besylate, fumarate, tartrate, succinate, citrate, lactate, pamoate, salicylate, stearate, methanesulfonate, p- toluenesulfonate, and oxalate, and the like. Suitable pharmaceutically acceptable salts also include those listed in Remington's Pharmaceutical Sciences, 17th Edition, pg. 1418 (1985) and P. Heinrich Stahl, Camille G. Wermuth (Eds.), Handbook of Pharmaceutical Salts Properties, Selection, and Use; 2002. Examples of acid addition salts include those formed from acids such as hydroiodic, phosphoric, metaphosphoric, nitric and sulfuric acids, and with organic acids, such as alginic, ascorbic, anthranilic, benzoic, camphorsulfuric, citric, embonic (pamoic), ethane-sulfonic, formic, fumaric, furoic, galacturonic, gentisic, gluconic, glucuronic, glutamic, glycolic, isonicotinic, isothionic, lactic, malic, mandelic, methanesulfonic, mucic, pantothenic, phenylacetic, propionic, saccharic, salicylic, stearic, succinic, sulfinilic, trifluoroacetic and arylsulfonic for example benzenesulfonic and p-toluenesulfonic acids. Examples of base addition salts formed with alkali metals and alkaline earth metals and organic bases include chloroprocaine, choline, N,N-dibenzylethylenediamine, diethanolamine; ethylenediamine, lysine, meglumaine (N-methylglucamine), and procaine, as well as internally formed salts. Salts having a non-physiologically acceptable anion or cation are within the scope of the disclosure as useful intermediates for the preparation of physiologically acceptable salts and/or for use in non-therapeutic, for example, in vitro, situations.

The disclosure specifically contemplates using salts of both ambrisentan and tadalafil and further contemplates mixtures of salts of tadalafil and/or ambrisentan.

In certain embodiments, the ambrisentan and/or tadalafil as used herein has not been sufficiently ionized and may be in the form a co-crystal. In one embodiment, the present disclosure provides a co-crystal composition comprising a co-crystal of ambrisentan and/or tadalafil, wherein said co-crystal comprises ambrisentan and/or tadalafil and a co-crystal former. The term "co-crystal" refers a crystalline material which comprises ambrisentan and/or tadalafil and one or more co-crystal formers, such as a pharmaceutically acceptable salt. In certain embodiments, the co-crystal can have an improved property as compared to the free form (i.e., the free molecule, zwitter ion, hydrate, solvate, etc.) or a salt (which includes salt hydrates and solvates). In further embodiments, the improved property is selected from the group consisting of: increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are well known to those of skill in the art.

The phrase "combination therapy", in defining use of a selective type-A endothelin receptor antagonist and a PDE5 inhibitor, is intended to embrace administration of each agent in a sequential manner in a regimen that will provide beneficial effects of the drug combination, and is intended as well to embrace co-administration of these agents in a substantially simultaneous manner, such as by oral ingestion of a single capsule having a fixed ratio of these active agents or ingestion of multiple, separate capsules for each agent. "Combination therapy" will also include simultaneous or sequential administration by intravenous, intramuscular or other parenteral routes into the body, including direct absorption through mucous membrane tissues, as found in the sinus passages. Sequential administration also includes drug combination where the individual elements may be administered at different times and/or by different routes but which act in combination to provide a beneficial effect, such as enhanced effectiveness.

In a particular embodiment, a combination therapy consists essentially of two active agents, namely, a selective type-A endothelin receptor antagonist and a PDE5 inhibitor.

In another embodiment, a combination therapy is a three-way combination comprising a selective type-A endothelin receptor antagonist, a PDE5 inhibitor and a third active agent effective for the treatment of the pulmonary hypertension condition or a condition related thereto. Illustratively and without limitation, the combination can include a third active agent selected from the group consisting of prostanoids, phosphodiesterase inhibitors other than tadalafil, endothelin receptor antagonists other than ambrisentan, calcium channel blockers, diuretics, anticoagulants, oxygen and combinations thereof.

The phrase "therapeutically-effective" is intended to qualify the amount of each agent for use in the combination therapy which will achieve the goal of improvement in pulmonary functions, while avoiding or reducing an adverse side effect typically associated with each agent. The therapeutically effective amount will vary depending upon the specific activity of the therapeutic agent being used, the severity of the patient's disease state, and the age, physical condition, existence of other disease states, and nutritional status of the patient. Additionally, other medication the patient may be receiving will effect the determination of the therapeutically effective amount of the therapeutic agent to administer.

"Co-action" means that the therapeutic effect of a PDE5 inhibitor such as tadalafil when administered in combination with a selective type-A endothelin receptor antagonist such as ambrisentan (or vice-versa) is greater than the sum of the therapeutic effects of the agents when administered separately. The term "therapeutic amount" used herein includes a less than standard therapeutic amount of one or both drugs, meaning that the amount required for the desired effect is lower than when the drug is used separately. A therapeutic amount also includes when one drug is given at a standard therapeutic dose and another drug is administered in a less than standard therapeutic dose. For example, ambrisentan could be given in a therapeutic dose and tadalafil could be given in a less than standard therapeutic dose to provide an enhanced result. In some embodiments, both drugs can be administered in a standard therapeutic dose for much greater efficacies.

The term "treatment" or "treating" means any treatment of a disease or condition in a subject, such as a mammal, including: 1) preventing or protecting against the disease or condition, that is, causing the clinical symptoms not to develop; 2) inhibiting the disease or condition, that is, arresting or suppressing the development of clinical symptoms; and/or 3) relieving the disease or condition that is, causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "susceptible" refers to a patient who has had at least one occurrence of the indicated condition.

The term "patient" typically refers to a "mammal" which includes, without limitation, human, monkeys, rabbits, mice, domestic animals, such as dogs and cats, farm animals, such as cows, horses, or pigs, and laboratory animals.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Intravenous administration" is the administration of substances directly into a vein, or "intravenously". Compared with other routes of administration, the intravenous (IV) route is the fastest way to deliver fluids and medications throughout the body. An infusion pump can allow precise control over the flow rate and total amount delivered, but in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used, which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream: however, a second fluid injection is sometimes used, a "flush", following the injection to push the medicine into the bloodstream more quickly.

"Oral administration" is a route of administration where a substance is taken through the mouth, and includes buccal, sublabial and sublingual administration, as well as enteral administration and that through the respiratory tract, unless made through, e.g., tubing so the medication is not in direct contact with any of the oral mucosa. Typical form for the oral administration of therapeutic agents includes the use of tablets or capsules.

2. Methods

Generally, the present disclosure relates to methods of treating or preventing pulmonary hypertension. The method comprises administration of therapeutic amounts of a selective type-A endothelin receptor antagonist (selective type-A ERA) and a phosphodiesterase type 5 inhibitor (PDE5 inhibitor). In a particular aspect, the method comprises administration of a therapeutic amount of tadalafil or a salt thereof and a therapeutic amount of ambrisentan or a salt thereof. In one embodiment, either one or both of ambrisentan or tadalafil are administered in an effective amount. The two agents may be administered separately or together in separate or a combined dosage unit. If administered separately, the ambrisentan may be administered before or after administration of the tadalafil.

As further discussed in the Examples, presented herewith is evidence of co-action of the combination of ambrisentan (AMB) and tadalafil (TAD) to relax endothelin-induced contractions and to inhibit hypoxia-induced pulmonary arterial pressure (PAP) in a pulmonary arterial hypertension (PAH) animal model. Such enhanced efficacy of the co-action is apparent as the combined effect is greater than the additive effects of mono-administration of each drug. In one aspect, such enhanced efficacy amounts to at least about 5% enhanced effectiveness over the additive effectiveness of mono-administration of each drug. Alternatively, such enhancement is at least about 10%, 15%, 20%, 25%, 30%, 35%, 40%, 45%, 50%, 55%, 60%, 65%, 70%, 80%, 90% or 100%. In other words, the combinations can achieve an effectiveness that is at least about 5%, or alternatively 10%, 15%, 20%, 25%, 30%, 35%, 40%, 45%, 50%, 55%, 60%, 65%, 70%, 80%, 90% or 100% greater than the sum of effectiveness of mono-administrations of either agent.

Figure 8:
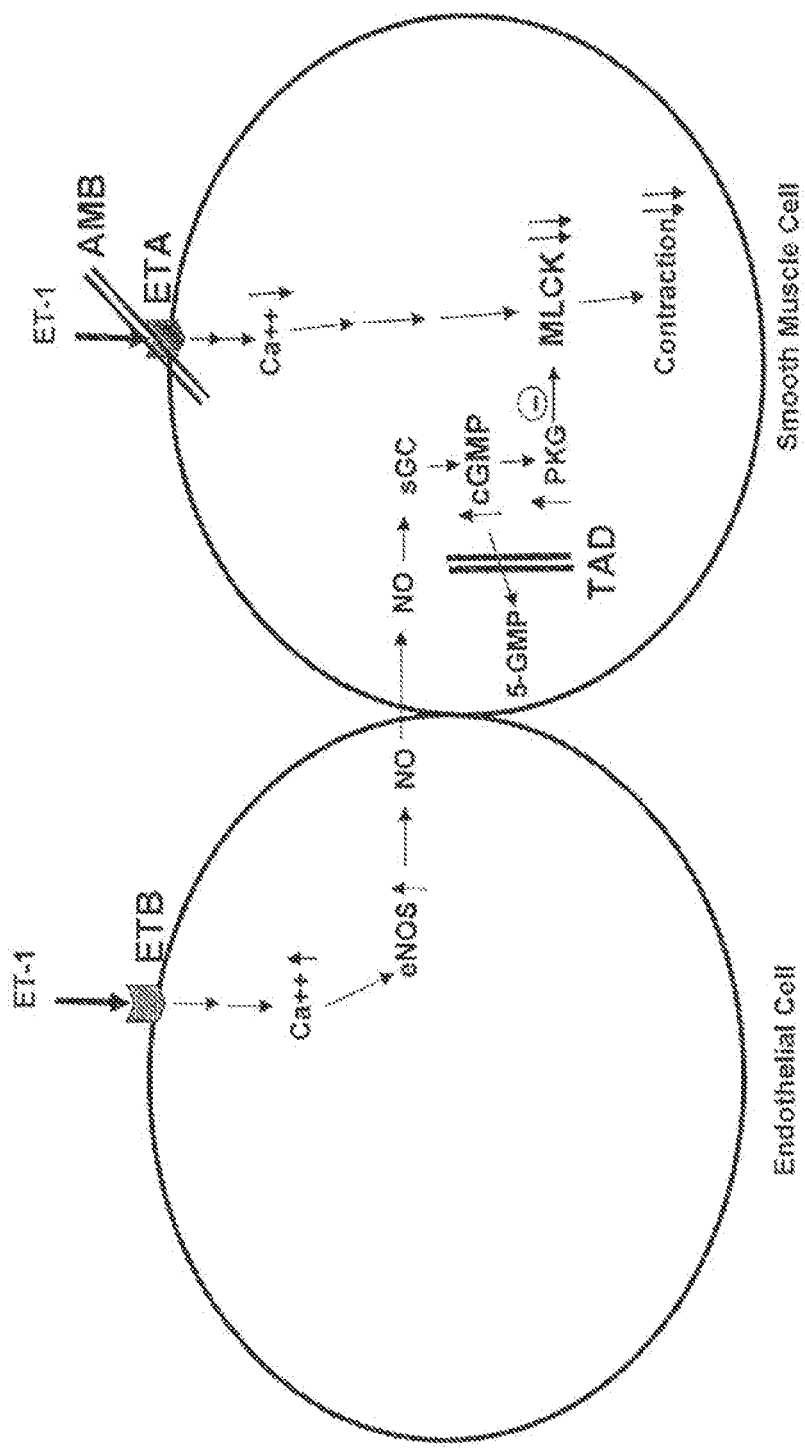
FIG. 8 illustrates the mechanism underlying the co-action between a selective type-A ERA and a PDE5 inhibitor that target vasorelaxation from two different pathways.
Figure 9:
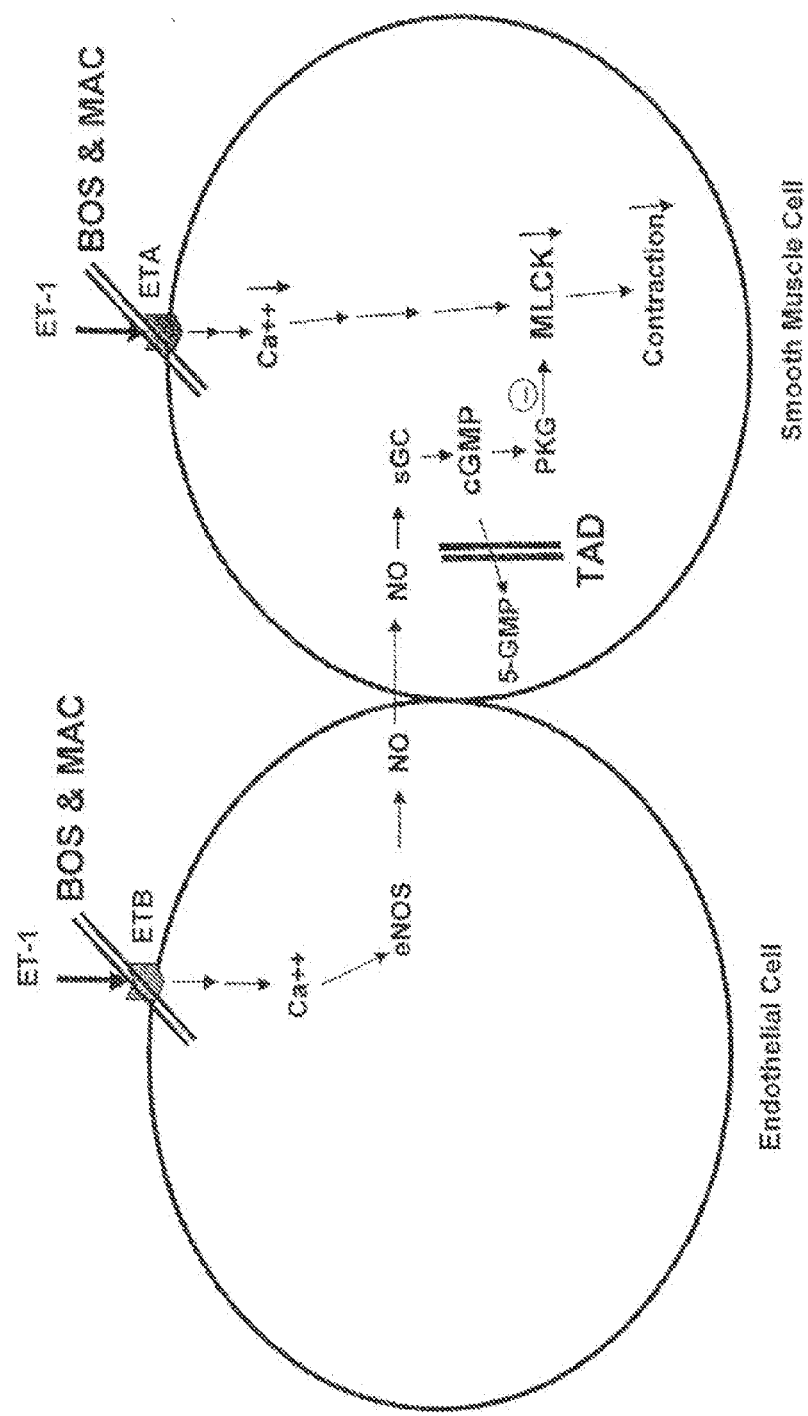
FIG. 9 illustrates the lack of beneficial co-action between a non-selective ERA or a selective type-B ERA and a PDE5 inhibitor that target the same pathway.

As demonstrated in the Examples, such an enhanced effect does not exist between TAD and a non-selective ERA such as bosentan (BOS) or macitentan (MAC). These results, therefore, suggest that type-B endothelin receptor in endothelium contributes to the enhanced effect of ambrisentan and tadalafil on vasorelaxation. As illustrated in FIGS. 8 and 9, the enhanced effect is due to ambrisentan and tadalafil co-acting in the endothelin receptor type-A and PDE5 pathways, respectively. Accordingly, similar enhanced effects are found between any selective type-A ERA and any PDE5 inhibitor. Additionally, a combination of a selective type-A ERA and a PDE5 inhibitor also results in enhanced effects in treating other diseases and conditions associated with the activity of endothelin receptor type-A.

As suggested by the above mechanism, the enhanced effect of the co-action of a selective type-A ERA and a PDE5 inhibitor depends on the amounts of each individual agent and/or ratios of such amounts. In one aspect, the ratio of the amount of the selective type-A ERA and the amount of the PDE5 inhibitor, in order to achieve such enhanced effects, can be from about 2:1, or alternatively 1:1, 1:1.5, 1:2, 1:2.5, 1:3, 1:4, 1:5, 1:6, 1:7, 1:8, 1:9 or 1:10 to about 1:3, or alternatively about 1:4, 1:5, 1:6, 1:7, 1:8, 1:9, 1:10, 1:11.1: 12, 1:15 or 1:20.

In one aspect, the ratio of amounts is a ratio of molar amounts of each agent. In another aspect, the ratio of amounts is a weight ratio of each agent.

In some embodiments, the ratio of the amount of the selective type-A ERA and the amount of the PDE5 inhibitor, in order to achieve enhanced effects, is around 1:3, which, for instance, can be from about 1:1.5 to about 1:5, or alternatively from about 1:2 to about 1:4. In one aspect, the selective type-A ERA is ambrisentan or a salt thereof. In one aspect, the PDE5 inhibitor is tadalafil or a salt thereof. In another aspect, the ratio is a weight ratio of each agent. In one aspect, the amount of ambrisentan or a salt thereof is from about 5 mg to about 10 mg daily for a human subject. In another aspect, the amount of tadalafil or a salt thereof is from about 15 mg to about 30 mg daily for a human subject.

In some embodiments, the ratio of the amount of the selective type-A ERA and the amount of the PDE5 inhibitor, in order to achieve enhanced effects, is around 1:1, which, for instance, can be from about 2:1 to about 1:2, or alternatively from about 1:1 to about 1:2. In one aspect, the selective type-A ERA is ambrisentan or a salt thereof. In one aspect, the PDE5 inhibitor is tadalafil or a salt thereof. In another aspect, the ratio is a weight ratio of each agent. In one aspect, the amount of ambrisentan or a salt thereof is from about 5 mg to about 10 mg daily for a human subject. In another aspect, the amount of tadalafil or a salt thereof is from about 5 mg to about 10 mg daily for a human subject.

In some embodiments, the ratio of the amount of the selective type-A ERA and the amount of the PDE5 inhibitor, in order to achieve enhanced effects, is around 1:10, which, for instance, can be from about 1:5 to about 1:15, or alternatively from about 1:8 to about 1:12. In one aspect, the selective type-A ERA is ambrisentan or a salt thereof. In one aspect, the PDE5 inhibitor is tadalafil or a salt thereof. In another aspect, the ratio is a weight ratio of each agent. In one aspect, the amount of ambrisentan or a salt thereof is from about 2 mg to about 5 mg daily for a human subject. In another aspect, the amount of tadalafil or a salt thereof is from about 20 mg to about 40 mg daily for a human subject.

In some embodiments, the ratio of the amount of the selective type-A ERA and the amount of the PDE5 inhibitor, in order to achieve enhanced effects, is around 1:4, which, for instance, can be from about 1:2 to about 1:7, or alternatively from about 1:3 to about 1:5. In one aspect, the selective type-A ERA is ambrisentan or a salt thereof. In one aspect, the PDE5 inhibitor is tadalafil or a salt thereof. In another aspect, the ratio is a weight ratio of each agent. In one aspect, the amount of ambrisentan or a salt thereof is from about 5 mg to about 10 mg daily for a human subject. In another aspect, the amount of tadalafil or a salt thereof is from about 30 mg to about 40 mg daily for a human subject.

In some embodiments, the ratio of the amount of the selective type-A ERA and the amount of the PDE5 inhibitor, in order to achieve enhanced effects, is around 1:8, which, for instance, can be from about 1:5 to about 1:10, or alternatively from about 1:7 to about 1:9. In one aspect, the selective type-A ERA is ambrisentan or a salt thereof. In one aspect, the PDE5 inhibitor is tadalafil or a salt thereof. In another aspect, the ratio is a weight ratio of each agent. In one aspect, the amount of ambrisentan or a salt thereof is from about 2 mg to about 5 mg daily for a human subject. In another aspect, the amount of tadalafil or a salt thereof is from about 30 mg to about 40 mg daily for a human subject.

Non-limiting examples of selective type-A ERA include ambrisentan and sitaxentan and salts thereof. In one aspect, the selective type-A ERA is ambrisentan. Examples of PDE5 inhibitors include, without limitation, tadalafil, avanafil, lodenafil, mirodenafil, sildenafil citrate, vardenafil and udenafil and salts thereof. In one aspect, the PDE5 inhibitor is tadalafil, Non-limiting examples of disease or condition associated with the activity of endothelin receptor type-A include hypertension, pulmonary hypertension, myocardial infarction, angina pectoris, acute kidney failure, renal insufficiency, cerebral vasospasms, cerebral ischemia, subarachnoid hemorrhages, asthma, atherosclerosis, intravascular coagulation, restenosis after angioplasty, hypertension caused by ischemia or intoxication, kidney failure caused by ischemia or intoxication, Raynaud's syndrome and asthmatic airway condition.

2.1 Pulmonary Hypertension (PH)

The pulmonary hypertension condition treated by the method of the disclosure, can comprise any one or more of the conditions recognized according to the World Health Organization (WHO) or Venice (2003) classification (see, for example. Rubin (2004) *Chest* 126:7-10) or the most recent Dana Point classification (Simonneau (2009) JACC 54; 54:S43-S54):

Group 1: Pulmonary arterial hypertension (PAH)
  1.1 idiopathic PAH
  1.2 familial PAH
  1.3 PAH associated with:
    1.3.1 collagen vascular disease
    1.3.2 congenital systemic-to-pulmonary shunts (including Eisenmenger's syndrome)
    1.3.3 portal hypertension
    1.3.4 HIV infection
    1.3.5 drugs and toxins
    1.3.6 other (thyroid disorders, glycogen storage disease, Gaucher disease, hereditary hemorrhagic telangiectasia, hemoglobinopathies, myeloproliferative disorders, splenectomy)
  1.4 PAH associated with significant venous or capillary involvement
    1.4.1 pulmonary veno-occlusive disease (PVOD)
    1.4.2 pulmonary capillary hemangiomatosis (PCH)

1.5 persistent pulmonary hypertension of the newborn
Group 2: Pulmonary hypertension with left heart disease
  2.1 left-sided atrial or ventricular heart disease
  2.2 left-sided valvular heart disease
Group 3: Pulmonary hypertension associated with lung diseases and/or hypoxemia
  3.1 chronic obstructive pulmonary disease (COPD)
  3.2 interstitial lung disease
  3.3 sleep-disordered breathing
  3.4 alveolar hypoventilation disorders
  3.5 chronic exposure to high altitude
  3.6 developmental abnormalities
Group 4: Pulmonary hypertension due to chronic thrombotic and/or embolic disease
  4.1 thromboembolic obstruction of proximal pulmonary arteries
  4.2 thromboembolic obstruction of distal pulmonary arteries
  4.3 non-thrombotic pulmonary embolism (tumor, parasites, foreign material)
Group 5: Miscellaneous (sarcoidosis, histiocytosis X, lymphangiomatosis, compression of pulmonary vessels (adenopathy, tumor, fibrosing mediastinitis))

In one aspect, the pulmonary hypertension condition comprises PAH (WHO Group 1), for example idiopathic PAH, familial PAH or PAH associated with another disease or condition.

Pulmonary hypertension at baseline can be mild, moderate or severe, as measured for example by WHO functional class, which is a measure of disease severity in patients with pulmonary hypertension. The WHO functional classification is an adaptation of the New York Heart Association (NYHA) system and is routinely used to qualitatively assess activity tolerance, for example in monitoring disease progression and response to treatment (Rubin (2004) Chest 126:7-10). Four functional classes are recognized in the WHO system:

Class I: pulmonary hypertension without resulting limitation of physical activity; ordinary physical activity does not cause undue dyspnea or fatigue, chest pain or near syncope;

Class II: pulmonary hypertension resulting in slight limitation of physical activity; patient comfortable at rest; ordinary physical activity causes undue dyspnea or fatigue, chest pain or near syncope;

Class III: pulmonary hypertension resulting in marked limitation of physical activity; patient comfortable at rest; less than ordinary activity causes undue dyspnea or fatigue, chest pain or near syncope;

Class IV: pulmonary hypertension resulting in inability to carry out any physical activity without symptoms; patient manifests signs of right-heart failure: dyspnea and/or fatigue may be present even at rest; discomfort is increased by any physical activity.

In one aspect, the subject at baseline exhibits pulmonary hypertension (e.g., PAH) of at least WHO Class I, for example WHO Class I, II or Class III.

In another aspect, the subject at baseline exhibits mean PAP at rest of at least about 30 mmHg, for example at least about 35, at least about 40, at least about 45 or at least about 50 mmHg.

The methods of the present disclosure, when applied to a subject, can achieve one or more of the following objectives:
  (a) adjustment of one or more hemodynamic parameters towards a more normal level, for example lowering mean PAP or PVR, raising cardiac output or index, or lowerin PCWP or LVEDP, versus baseline;
  (b) improvement of pulmonary function versus baseline, for example increasing exercise capacity or activity, illustratively as measured in a test of 6-minute walking distance (6MWD) or measure of activity, or lowering Borg dyspnea index (BDI);
  (c) improvement of one or more quality of life parameters versus baseline, for example an increase in score on at least one of the SF-36® health survey functional scales;
  (d) general improvement versus baseline in the severity of the condition, for example by movement to a lower WHO functional class;
  (e) improvement of clinical outcome following a period of treatment, versus expectation in absence of treatment (e.g., in a clinical trial setting, as measured by comparison with placebo), including improved prognosis, extending time to or lowering probability of clinical worsening, extending quality of life (e.g., delaying progression to a higher WHO functional class or slowing decline in one or more quality of life parameters such as SF-36® health survey parameters), and/or increasing longevity; and/or
  (f) adjustment towards a more normal level of one or more molecular markers that can be predictive of clinical outcome (e.g., plasma concentrations of endothelin-1 (ET-1), cardiac troponin T (cTnT) or B-type natriuretic peptide (BNP)).

What constitutes a therapeutically effective amount for treating PH, or in particular, PAH, can vary depending on the particular pulmonary hypertension condition to be treated, the severity of the condition, body weight and other parameters of the individual subject, and can be readily established without undue experimentation by the physician or clinician based on the disclosure herein.

Various clinical parameters and standards to measure the effectiveness of a PH therapy are described below and are known in the art as well. Accordingly, the effectiveness of a PH therapy, such as that of any combination formulation of the present disclosure, can be measured by these parameters or standards. Additionally, the relative effectiveness of a therapy, such as that of a combination of two agents, as compared to the effectiveness of mono-administrations of each agent, can be determined with these clinical parameters or standards, as well as in a non-clinical setting. Examples of such non-clinical settings include, without limitation, an in vitro assay or animal study. Non-limiting examples of in vitro assays are provided in Examples.

A. Improvement on Clinical Parameters

In one aspect, the subject being treated experiences, during or following the treatment period, at least one of
  (a) adjustment of one or more hemodynamic parameters indicative of the pulmonary hypertension condition towards a more normal level versus baseline;
  (b) increase in exercise capacity versus baseline;
  (c) lowering of BDI versus baseline;
  (d) improvement of one or more quality of life parameters versus baseline; and/or
  (e) movement to a lower WHO functional class.

Any suitable measure of exercise capacity can be used; a particularly suitable measure is obtained in a 6-minute walk test (6MWT), which measures how far the subject can walk in 6 minutes, i.e., the 6-minute walk distance (6MWD).

The Borg dyspnea index (BDI) is a numerical scale for assessing perceived dyspnea (breathing discomfort). It measures the degree of breathlessness after completion of the 6 minute walk test (6MWT), where a BDI of 0 indicates no breathlessness and 10 indicates maximum breathlessness.

In various aspects, an effective amount of a PH therapy adjusts one or more hemodynamic parameters indicative of the pulmonary hypertension condition towards a more normal level. In one such aspect, mean PAP is lowered, for example by at least about 3 mmHg, or at least about 5 mmHg, versus baseline. In another such aspect, PVR is lowered. In yet another such aspect, PCWP or LVEDP is raised.

In various aspects, an effective amount of a PH therapy improves pulmonary function versus baseline. Any measure of pulmonary function can be used; illustratively 6MWD is increased or BDI is lowered.

In one such aspect, 6MWD is increased from baseline by at least about 10 m, for example at least about 20 m or at least about 30 m. In many instances, the method of the present embodiment will be found effective to increase 6MWD by as much as 50 m or even more.

In another such aspect, BDI, illustratively as measured following a 6MWT, is lowered from baseline by at least about 0.5 index points. In many instances, the method of the present embodiment will be found effective to lower BDI by as much as 1 full index point or even more.

The SF-36® health survey provides a self-reporting, multi-item scale measuring eight health parameters: physical functioning, role limitations due to physical health problems, bodily pain, general health, vitality (energy and fatigue), social functioning, role limitations due to emotional problems, and mental health (psychological distress and psychological well-being). The survey also provides a physical component summary and a mental component summary.

In various aspects, an effective amount of a PH therapy can improve quality of life of the subject, illustratively as measured by one or more of the health parameters recorded in an SF-36® survey. For example, an improvement versus baseline is obtained in at least one of the SF-36 physical health related parameters (physical health, role-physical, bodily pain and/or general health) and/or in at least one of the SF-36 mental health related parameters (vitality, social functioning, role-emotional and/or mental health). Such an improvement can take the form of an increase of at least 1, for example at least 2 or at least 3 points, on the scale for any one or more parameters.

B. Improvement of Prognosis

In another embodiment, the treatment method of the present disclosure can improve the prognosis for a subject having a pulmonary hypertension condition. The treatment of this embodiment can provide (a) a reduction in probability of a clinical worsening event during the treatment period, and/or (b) a reduction from baseline in serum brain natriuretic peptide (BNP) or NT pro-BNP or its N-terminal prohormone, NT-pro-BNP concentration, wherein, at baseline, time from first diagnosis of the condition in the subject is not greater than about 2 years.

Time from first diagnosis, in various aspects, can be, for example, not greater than about 1.5 years, not greater than about 1 year, not greater than about 0.75 year or not greater than about 0.5 year. In one aspect, administration of ambrisentan can begin substantially immediately, for example, within about one month or within about one week, upon diagnosis.

In this embodiment, the treatment period is long enough for the stated effect to be produced. Typically, the longer the treatment continues the greater and more lasting will be the benefits. Illustratively, the treatment period can be at least about one month, for example at least about 3 months, at least about 6 months or at least about 1 year. In some cases, administration can continue for substantially the remainder of the life of the subject.

Clinical worsening event (CWEs) include death, lung transplantation, hospitalization for the pulmonary hypertension condition, atrial septostomy, initiation of additional pulmonary hypertension therapy or an aggregate thereof. Therefore, the treatments of the present disclosure can be effective to provide a reduction of at least about 25%, for example at least about 50%, at least about 75% or at least about 80%, in probability of death, lung transplantation, hospitalization for pulmonary arterial hypertension, atrial septostomy and/or initiation of additional pulmonary hypertension therapy during the treatment period.

Time to clinical worsening of the pulmonary hypertension condition is defined as the time from initiation of an ambrisentan treatment regime to the first occurrence of a CWE.

In another particular aspect, the method is effective to provide a reduction from baseline of at least about 15%, for example at least about 25%, at least about 50% or at least about 75%, in BNP or NT-pro-BNP concentration.

The pulmonary hypertension condition according to this embodiment can comprise any one or more of the conditions in the WHO, Venice (2003) or Dana Point (2009) classifications described above. In one aspect, the condition comprises PAH (WHO Group 1), for example idiopathic PAH, familial PAH or PAH associated with another disease.

In various aspects of this embodiment, the subject at baseline exhibits PH (e.g., PAH) of WHO Class I-IV, for example Class I, Class II, Class III or Class IV as described above.

In a more particular embodiment, the subject at baseline has a resting PAP of at least about 25 mmHg, for example at least about 30 mmHg, at least about 35 mmHg or at least about 40 mmHg.

In various aspects of this embodiment, the subject can experience, during or following the treatment period, at least one of:

(a) adjustment of one or more hemodynamic parameters indicative of improvement of the cardiopulmonary hypertension condition towards a more normal level versus baseline;

(b) improvement in cardiopulmonary function; illustratively an increase in exercise capacity or surrogate thereof (e.g., CPET measures such as $VO_2$ peak. $VE/VCO_2$, $PETCO_2$ and the like) or lowering of BDI versus baseline;

(c) improvement of one or more quality of life parameters versus baseline; and/or (d) maintenance of or movement to a lower WHO functional class.

For example, in one aspect the subject can experience improvement in cardiopulmonary function versus baseline. Any measure of cardiopulmonary function can be used; illustratively 6MWD is increased or BDI is lowered.

In one such aspect, 6MWD is improved from baseline by at least about 10 m, for example, at least about 20 m or at least about 30 m. In many instances, the method of the present embodiment will be found effective to increase 6MWD by as much as 50 m or even more.

In another such aspect, BDI, illustratively as measured following a 6MWT, is lowered from baseline by at least about 0.5 point. In many instances, the method of the present embodiment will be found effective to lower BDI by as much as 1 full index point or even more.

In another aspect, the subject can experience improvement in quality of life, illustratively as measured by one or more of the health parameters recorded in an SF-36® survey. For example, an improvement versus baseline can be obtained in at least one of the SF-36 physical health related parameters (physical health, role-physical, bodily pain and/or general health) and/or in at least one of the SP-35 mental health related parameters (vitality, social functioning, role-emotional and/or mental health). Such an improvement can take the form of an increase of at least 1, for example at least 2 or at least 3 points, on the scale for any one or more parameters.

In another aspect, the subject can experience maintenance or improvement in WHO functional class.

C. Prolongation of Life

In yet another embodiment, the treatment methods of the present disclosure can prolong the life of a subject having a pulmonary hypertension condition, from a time of initiation of treatment, by at least about 30 days, Variants and illustrative modalities of this method are as set forth above.

D. Extending Time to Clinical Worsening

Still in another embodiment, the present methods can extend time to clinical worsening in a subject having a pulmonary hypertension condition, and decrease the probability of a clinical worsening event by at least about 25%. Variants and illustrative modalities of this method are as set forth above.

B. Other Treatment Objectives

In any of the methods described hereinabove, the subject can be male or female. For example, the combined drugs can be administered to a female subject according to any of the above methods, including the indicated variants and illustrative modalities thereof. Alternatively, ambrisentan can be administered to a male subject, for example a reproductively active male subject, according to any of the above methods, including the indicated variants and illustrative modalities thereof.

In another embodiment, the methods provided herein are useful for treating a pulmonary hypertension condition in a reproductively active male subject, wherein fertility of the subject is not substantially compromised. "Not substantially compromised" in the present context means that spermatogenesis is not substantially reduced by the treatment and that no hormonal changes are induced that are indicative of or associated with reduced spermatogenesis. Male fertility can be assessed directly, for example, by sperm counts from semen samples, or indirectly by changes in hormones such as follicle stimulating hormone (FSH), luteinizing hormone (LH), inhibin B and testosterone.

In one embodiment, a method is provided for treating PAH in a subject, wherein the PAH is associated with one or more of (a) a congenital heart defect, (b) portal hypertension, (c) use of a drug or toxin other than an anorexigen, (d) thyroid disorder, (e) glycogen storage disease, (f) Gaucher disease, (g) hereditary hemorrhagic telangiectasia, (h) hemoglobinopathy, (i) myeloproliferative disorder, (j) splenectomy, (k) pulmonary veno-occlusive disease and/or (l) pulmonary capillary hemangiomatosis. Variants and illustrative modalities of this method are as set forth hereinabove.

Further, in another embodiment, a method is provided for treating a pulmonary hypertension condition classified in WHO Groups 2-5 in a subject. Variants and illustrative modalities of this method are as set forth hereinabove. In one aspect, the condition comprises left-sided atrial or ventricular heart disease and/or left-sided valvular heart disease. In another aspect, the condition is associated with one or more of chronic obstructive pulmonary disease (COPD), interstitial lung disease (ILD), sleep-disordered breathing, an alveolar hypoventilation disorder, chronic exposure to high altitude, a developmental abnormality, thromboembolic obstruction of proximal and/or distal pulmonary arteries, a non-thrombotic pulmonary embolism, sarcoidosis, histiocytosis X, lymphangiomatosis, and/or compression of pulmonary vessels.

2.3 Other Uses of the Combinations

Increased or abnormal release of endothelin causes persistent vasoconstriction in the peripheral, renal and cerebral blood vessels, which may lead to illnesses. It has been reported in the literature that elevated plasma levels of endothelin were found in patients with hypertension, acute myocardial infarct, pulmonary hypertension, Raynaud's syndrome, atherosclerosis and in the airways of asthmatics (see. e.g., U.S. Pat. No. 7,601,730). Accordingly, substances which specifically inhibit the binding of endothelin to the receptor ought also to antagonize the various abovementioned physiological effects of endothelin and therefore be valuable drugs, such as ambrisentan and tadalafil. Likewise, the combination of such drugs can also be effective in treating such diseases and conditions.

Thus, in one aspect, the present disclosure provides a method for treating or preventing a disease in a patient in need thereof comprising administering to the patient therapeutic amounts of a selective type-A ERA and a PDE5 inhibitor, wherein the disease is selected from the group consisting of hypertension, pulmonary hypertension, myocardial infarction, angina pectoris, acute kidney failure, renal insufficiency, cerebral vasospasms, cerebral ischemia, subarachnoid hemorrhages, asthma, atherosclerosis, intravascular coagulation, restenosis after angioplasty, hypertension caused by ischemia or intoxication, kidney failure caused by ischemia or intoxication, Raynaud's syndrome and asthmatic airway condition.

Also provided is a method for inhibiting vasoconstriction in a patient in need thereof comprising administering to the patient therapeutic amounts of ambrisentan and tadalafil or pharmaceutically acceptable salt thereof. In one aspect, the vasoconstriction is endothelin-induced.

It is also contemplated that by combining ambrisentan and tadalafil any undesired side effects may be reduced. For example, administration of ambrisentan to a patient already receiving tadalafil therapy reduces the side effects of tadalafil. The co-action effect of combined administration will allow for a reduction in amount of tadalafil necessary to achieve a therapeutic effect, thereby resulting in a reduced incidence of undesirable side effects. As such, in one embodiment, the disclosure is directed to a method for reducing the undesirable side effects of tadalafil or a salt thereof comprising administering a therapeutic amount of ambrisentan or a salt thereof.

As discussed above, by administration of ambrisentan, the therapeutically effective amount of tadalafil is reduced. As such, the disclosure, in one embodiment, is directed to a method for reducing the therapeutically effective dose of tadalafil or a salt thereof comprising administering to a patient a therapeutic amount of ambrisentan or a salt thereof.

2.3 Dosing

For all of the methods just described, at least one of either ambrisentan or a salt thereof or tadalafil or a salt thereof is administered in a less than standard therapeutic dose which becomes therapeutically effective as a consequence of its administration with the other drug. However, it is also contemplated that tadalafil and ambrisentan may also both be administered in a therapeutically effective amount. In some embodiments, the tadalafil is administered in an effective dose and ambrisentan is administered in a standard therapeutically effective dose. In other embodiment, ambrisentan is administered in a less than standard therapeutic dose and tadalafil is administered in a standard therapeutically effective dose. In still other embodiments, both ambrisentan and tadalafil are administered in less than standard therapeutic doses. The expression "therapeutic amounts of tadalafil and ambrisentan or a salt thereof" is intended to encompass all possible combinations of standard and less than standard therapeutic doses of ambrisentan and its therapeutically acceptable salt and tadalafil or its therapeutically acceptable salt.

In some embodiments, tadalafil or a salt thereof and ambrisentan or a salt thereof are administered separately or sequentially within a time period effective to provide enhanced efficacy.

Ambrisentan and tadalafil may be given to the patient in either single or multiple doses by any of the accepted modes of administration of agents having similar utilities, for example as described in those patents and patent applications incorporated by reference, including buccal, by intra-arterial injection, intravenously, intraperitoneally, parenterally, intramuscularly, subcutaneously, orally, or via an impregnated or coated device such as a stent, for example, or an artery-inserted cylindrical polymer. In one embodiment, ambrisentan or a salt thereof and tadalafil or a salt thereof are administered intravenously.

In one embodiment, ambrisentan or a salt thereof and tadalafil or a salt thereof are administered orally. Tadalafil or a salt thereof and ambrisentan or a salt thereof may also be administered as a combined dosage unit, such as, for example, in a tablet.

As mentioned above, tadalafil or a salt thereof and ambrisentan or a salt thereof may be administered in a therapeutic amount or an effective amount. Therefore, in some embodiments, the amount of ambrisentan or a salt thereof administered is from about 0.5 mg to about 100 mg daily or from about 1 mg to about 100 mg daily, or from about 2 mg to about 50 mg daily, or from about 2 mg to about 20 mg daily. Further, the amount of tadalafil or a salt thereof administered is from about 1 mg to about 500 mg daily or from about 5 mg to about 500 mg daily, or from about 5 mg to about 200 mg daily, or from about 10 mg to about 200 mg daily, or from about 10 mg to about 100 mg daily. These aggregate daily doses may be administered to the patient either once or twice a day.

In one embodiment, whether ambrisentan and tadalafil are administered together or separately, the ratio of the amount of ambrisentan or a salt thereof and the amount of tadalafil or a salt thereof can be in a range from about 1:1 to about 1:10, or alternatively from about 1:1 to about 1:8, or alternatively from about 1:2 to about 1:5, or alternatively from about 1:2.5 to about 1:3.5 or in a particular aspect, is about 1:3.

Additionally, ambrisentan or a salt thereof is administered as a sustained release formulation and/or tadalafil or a salt thereof is administered as an immediate release or sustained release formulation. This is more thoroughly discussed in the next section.

In one embodiment then, the patient under treatment is already taking a maintenance dose of tadalafil ranging from 20 to 40 mg with a typical dose once daily. To this dosing regimen is then added ambrisentan at from about 5 mg to about 10 mg. By administering such therapeutic doses of ambrisentan the amount of tadalafil can then be decreased to from about 20-40 to about 15-30 mg or about 10-20 mg daily thereby greatly reducing the incidence of adverse events.

Likewise, by administering such therapeutic doses of tadalafil the amount of ambrisentan can then be decreased to from about 5-10 to about 3-8 mg or about 2-5 mg daily thereby greatly reducing the incidence of adverse events.

3. Active Ingredients and Compositions 3.1 Pharmaceutical Formulations

As mentioned above, a combination of tadalafil and ambrisentan may be formulated separately. The separate dosage forms containing each active ingredient can be administered sequentially or at similar times (i.e., either together or one after the other). In another embodiment, tadalafil and ambrisentan is co-formulated into a combined dosage unit. Accordingly, in one embodiment, the disclosure is directed to pharmaceutical formulations comprising a therapeutic amount of tadalafil or a salt thereof, a therapeutic amount of ambrisentan or a salt thereof, and a pharmaceutically acceptable carrier.

In another embodiment, the formulation comprises an effective amount of ambrisentan or a salt thereof and/or tadalafil or a salt thereof. In certain embodiments, the formulations are formulated for either intravenous or oral administration. In still other embodiment, the two active ingredients are co-formulated into a combined dosage unit. In still yet other embodiments, the two active ingredients are formulated separately for co-therapy administration.

3.2 Co-formulations

In certain embodiments of the present disclosure, the ambrisentan and tadalafil are co-formulated into a combined dosage unit or unitary dosage form suitable for oral administration. In certain embodiments, the ambrisentan is formulated as a sustained release formulation. In certain embodiments, the tadalafil is formulated for immediate release or sustained release.

In one embodiment, the formulation is in tablet form or capsule form. In embodiment, the tablet or capsule comprises from about 1 mg to about of 500 mg of tadalafil or a pharmaceutically acceptable salt thereof. In another embodiment, the tablet or capsule comprises from about 5 mg to about 500 mg of tadalafil or a pharmaceutically acceptable salt thereof. In yet another embodiment, the tablet or capsule comprises from about 5 mg to about 200 mg of tadalafil or a pharmaceutically acceptable salt thereof. In still yet another embodiment, the tablet or capsule comprises from about 10 mg to about 200 mg of tadalafil or a pharmaceutically acceptable salt thereof. In still yet another embodiment, the tablet or capsule comprises from about 10 mg to about 100 mg of tadalafil or a pharmaceutically acceptable salt thereof.

In one embodiment, the tablet or capsule comprises from about 0.5 mg to about 100 mg of ambrisentan or a pharmaceutically acceptable salt thereof. In another embodiment, the tablet or capsule comprises from about 1 mg to about 100 mg of ambrisentan or a pharmaceutically acceptable salt thereof. In yet another embodiment, the tablet or capsule comprises from about 2 mg to about 50 mg of ambrisentan or a pharmaceutically acceptable salt thereof. In yet another embodiment, the tablet or capsule comprises from about 2 mg to about 20 mg of ambrisentan or a pharmaceutically acceptable salt thereof.

In one embodiment, the ratio of the amount of ambrisentan or a salt thereof and the amount of tadalafil or a salt thereof, in the formulation, can be from about 1:1 to about 1:10, or alternatively from about 1:1 to about 1:8, or alternatively from about 1:2 to about 1:5, or alternatively from about 1:2.5 to about 1:3.5 or in a particular aspect, is about 1:3.

In one such embodiment, the ambrisentan composition is placed in a portion of the tablet which is separate from, but in contact with, the portion of the tablet containing the tadalafil composition. It will be understood that the unitary dosage form may comprise simply compressing the ambrisentan composition and the tadalafil composition into a multilayer tablet or conventionally processed into other conventional unitary dosage forms such as a capsules. The multilayer tablets and capsules suitable for use in the present disclosure can be fabricated using methods known in the art using standard machinery.

The tablets may comprise two layers, i.e. a first layer which comprises the tadalafil and is formulated for immediate release or sustained release, and a second layer which comprises the ambrisentan and is formulated for sustained release. Alternatively, the multilayer tablet may comprise an inner layer and an outer layer, where the inner layer comprises the sustained release ambrisentan formulation and where the outer layer comprises the immediate release or sustained release tadalafil layer. In another embodiment, the ambrisentan and tadalafil are co-formulated into a capsule, where the capsule allows for the immediate release or sustained release of tadalafil and the sustained release of ambrisentan. For example, the capsule may contain granules of both tadalafil and ambrisentan, where the granules have been formulated such that the tadalafil is available for immediate release or sustained release and the Ambrisentan is formulated for sustained release. Alternatively, the capsule may contain a liquid immediate release or sustained release formulation of tadalafil and a solid sustained release formulation of ambrisentan. However, such embodiments are exemplary and are not intended to limit the formulations of the present disclosure.

A multilayer tablet can be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active agent or dispersing agent. Molded tablets may be made by molding in a suitable machine a mixture of the powdered active ingredient moistened with an inert liquid diluent. The tablets may optionally be coated or scored.

The tablets may contain one or more agents including sweetening agents, flavoring agents, coloring agents and preserving agents, in order to provide a palatable preparation. Tablets containing the active ingredients in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay-material such as glyceryl monostearate or glyceryl distearate alone or with a wax may be employed.

3.3 Additional Formulations

Formulations also contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. The same formulations are contemplated for separate administration of ambrisentan and tadalafil.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The ideal forms of the apparatus for administration of the novel combinations for pulmonary hypertension and other methods of the disclosure consist therefore of (1) either a syringe comprising 2 compartments containing the 2 active substances ready for use or (2) a kit containing two syringes ready for use.

In making a pharmaceutical composition including ambrisentan and tadalafil, the active ingredients are usually diluted by an excipient or carrier and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure can be formulated so as to provide quick, sustained or delayed release of the active ingredient after administration to the patient by employing procedures known in the art. As discussed above, given the reduced bioavailabity of ambrisentan, sustained release formulations are generally preferred. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345.

The compositions are preferably formulated in a unit dosage form. The term "unit dosage forms" or "combined dosage unit" refers to physically discrete units suitable as unitary dosages for human subjects and other mammals, each unit containing a predetermined quantity of the active materials calculated to produce the desired therapeutic effect, in association with a suitable pharmaceutical excipient (e.g., a tablet, capsule, ampoule). The active agents of the disclosure are effective over a wide dosage range and are generally administered in a pharmaceutically effective amount. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredients are mixed with a pharmaceutical excipient to form a solid preformulation composition containing a homogeneous mixture of a compound of the present disclosure. When referring to these preformulation compositions as homogeneous, it is meant that the active ingredients are dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage element, the latter being in the form of an envelope over the former. Ambrisentan and the co-administered agent(s) can be separated by an enteric layer that serves to resist disintegration in the stomach and permit the inner element to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Additional embodiments of the disclosure include kits comprising a therapeutic amount of ambrisentan or a salt thereof and a therapeutic amount of tadalafil or a salt thereof.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLES

Tadalafil as used in this disclosure is commercially available and can be prepared by conventional methods such as in the manner disclosed in U.S. Pat. No. 5,859,006. Ambrisentan is also commercially available or may be prepared by conventional methods such as in the manner disclosed in U.S. Pat. No. 5,703,017. The entire disclosure of both patents is hereby incorporated by reference. Additionally, the abbreviations used throughout have the following meanings:

μM=micromolar
μm=micrometer
cm=centimeter
kg=kilogram
mA=milliamp
min=minute
mm=millimeter
mM=millimolar
mpk=milligram per kilogram (body weight)
ms=millisecond
nM=nanomolar
AMB=ambrisentan
TAD=tadalafil
BOS=bosentan
MAC=macitentan
ET-1=endothelin-1

Example 1

Ambrisentan and Tadalafil Relax Endothelin-induced Contraction of Rat Pulmonary Arteries and Aortas This example examines the pharmacological effects of the combination of ambrisentan and tadalafil in comparison with either of them alone, with respect to their capability to relax isolated rat pulmonary artery and thoracic aorta preparations.

The selective type-A endothelin receptor antagonist, ambrisentan (Letairis®), and the phosphodiesterase type 5 inhibitor, tadalafil (Adcirca®), are currently used to treat pulmonary arterial hypertension. Isolated rat intact intrapulmonary arterial rings contracted with 8 nM endothelin-1 (ET-1) were relaxed by 10 nM ambrisentan (from Gilead Sciences, Inc.) and 30 nM tadalafil (from Sequoia Research Products Ltd. Pangbourne, UK) by 30±13% (mean±SEM, n=3) and 12±5% (n=3), respectively, whereas both drugs in combination relaxed the intact intrapulmonary arterial rings by 77±1:5% (FIG. 1, n=3, P<0.01 vs. mono-administration of ambrisentan or tadalafil).

Similarly, mono-administration of 10 nM ambrisentan and 30 nM tadalafil relaxed isolated rat intact thoracic aortic rings in the presence of 8 nM ET-1 by 32±3% (n=3) and 16±4% (n=3), respectively. The combination of both 10 nM ambrisentan and 30 nM tadalafil relaxed the ET-1-induced contraction of the intact thoracic aortic rings by 81±7% (FIG. 1, n=3; P<0.01 vs. mono-administration of ambrisentan or tadalafil). The $IC_{50}$ value for tadalafil to relax ET-1 constricted aortic rings was reduced from 79 nM to 16 nM in the presence of 10 nM ambrisentan.

In endothelium-denuded aortic rings, tadalafil failed to inhibit contraction induced by ET-1 whereas 10 nM ambrisentan reduced contraction by 26±7% (n=4); the drug combination was not more effective than mono-administration of ambrisentan.

These data suggest that the combination of ambrisentan and tadalafil inhibit endothelin-induced vasoconstriction and endothelium is required to produce their enhanced effect on vasorelaxation.

Example 2

Selective Type-A ERA and PDE5 Inhibitor Shows Co-action in Relaxing Endothelin-induced Contraction of Pulmonary Arteries while Non-selective ERA and PDE5 Inhibitor Lack Such Co-action This Example confirms the beneficial co-action of ambrisentan and tadalafil as observed in Example 1 and further investigates the mechanism underlying such co-action.

Ambrisentan (Letairis®) is a selective type-A endothelin receptor antagonist approved for treatment of PAH. Bosentan (Tracleer®) is a non-selective (types A&B) endothelin receptor antagonist for PAH. Macitentan (second generation of Bosentan) is a non-selective endothelin receptor antagonist in phase III for PAH. Tadalafil (Adcirca® and Cialis®) is a PDE5 inhibitor for PAH and erectile dysfunction (ED).
Method: Ex-vivo Vascular Function Assay Intrapulmonary arteries (200-500 μm) and aortas were isolated from Sprague Dawley rats (300-320 g) and cut into 1-2 mm rings. Rings were mounted in a myograph and constricted with a submaximal concentration (8 nM) of ET-1. Ambrisentan, Bosentan, Macitentan and Tadalafil alone and in combination were evaluated in ET-constricted rings.
Results:

FIG. 2 shows the effects of Tadalafil with Ambrisentan, Bosentan or Macitentan to attenuate ET-1-induced contraction of rat pulmonary artery rings.

Isolated rat intact intrapulmonary arterial rings contracted with 8 nM endothelin-1 (ET-1) were relaxed by 10 nM ambrisentan and 30 nM tadalafil by 29±1% (mean±SEM, n=4) and 22±2% (n=4), respectively, whereas both drugs in combination relaxed the intact intrapulmonary arterial rings by 85±3% (FIG. 2, n=4, P<0.01 vs. mono-administration of ambrisentan or tadalafil).

In contrast, the combination of 30 nM tadalafil with 100 nM bosentan or 30 nM macitentan, two nonselective type-A & B endothelin receptor antagonists, relaxed the ET-1-dependent contraction of the intact intrapulmonary arterial rings by 50±4% (FIG. 2, n=4, P<0.05 vs. mono-administrations of bosentan and tadalafil or combination of ambrisentan with tadalafil) or 48±8% (FIG. 2, n=7, P<0.05 vs. mono-administrations of macitentan and tadalafil or combination of ambrisentan with tadalafil). Mono-administrations of 100 nM bosentan and 30 nM macitentan produced a vasorelaxant effect similar to 10 nM ambrisentan and relaxed the isolated intact intrapulmonary arterial rings contracted with 8 nM ET-1 by 25±1% (n=4) and 31±2% (n=4), respectively.

Figure 3:
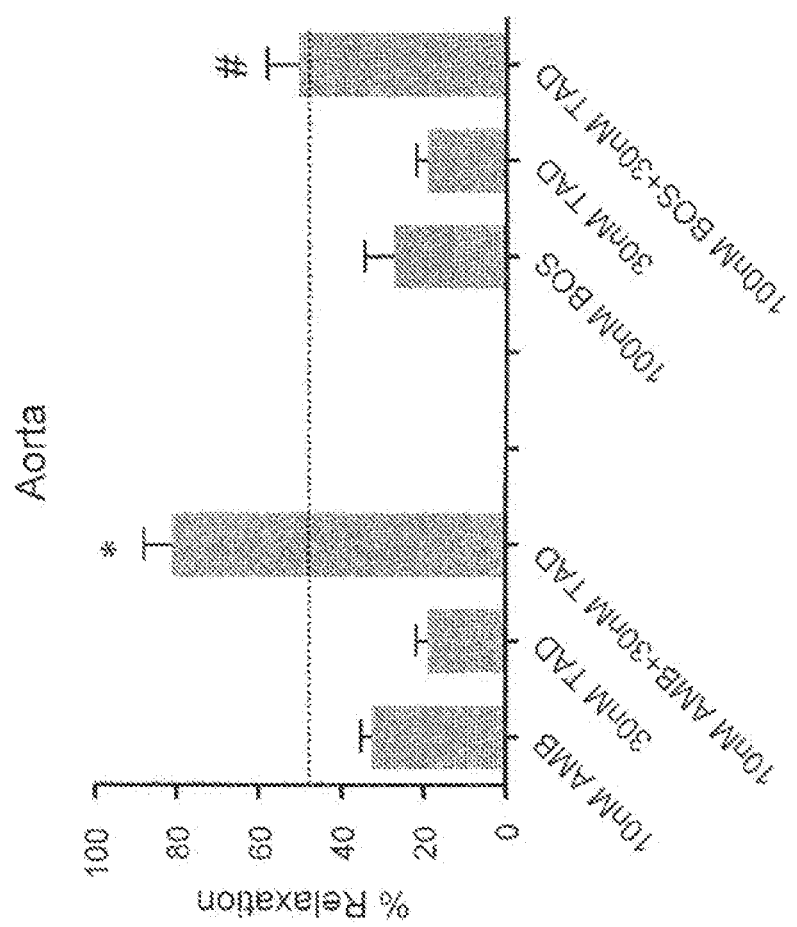
FIG. 3 shows the effects of TAD with AMB or BOS to attenuate ET-1-induced contraction of rat aortic rings. Data are expressed as mean±SEM. *$p<0.01$ vs. 10 nM AMB or 30 nM TAD. #$p<0.05$ vs. 100 nM BOS or 30 n M TAD. ---: represents the additive effect of AMB with TAD. The data show that the effect of the combination of AMB and TAD is greater than the additive effects of each drug (indicated by the dotted line), whereas the combinatory effect of BOS and TAD is not.

FIG. 3 shows the effects of TAD with AMB or BOS to attenuate ET-1-induced contraction of rat aortic rings. Again, the effect of the combination of AMB and TAD was almost double of the sum of mono-administration of each drug. In contrast, such enhanced effectiveness was not observed for the combination of TAD and BOS.

Figure 4:
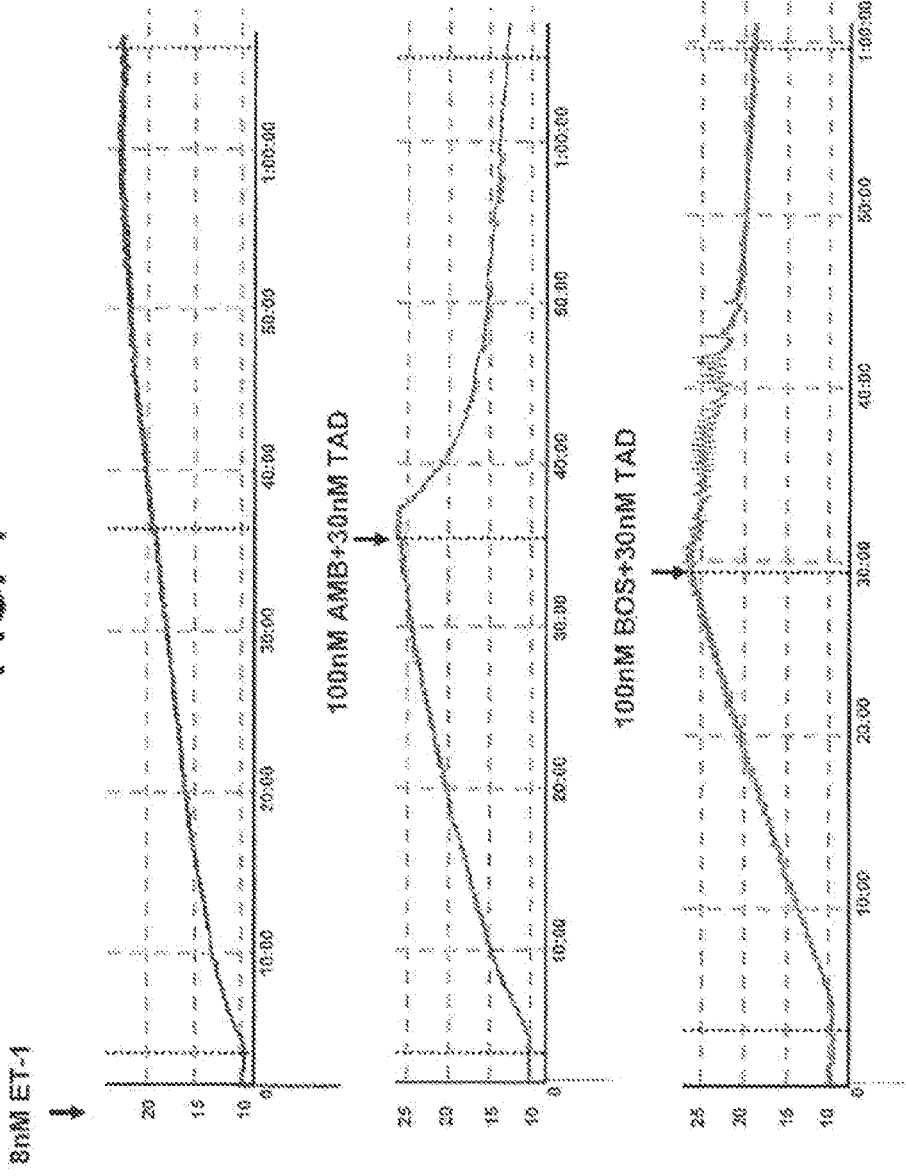
FIG. 4 are contraction graphs showing the effects of TAD in combination with AMB or BOS on ET-1-induced contraction of rat aortic rings (top: no treatment; middle: AMB+TAD; bottom: BOS+TAD). It is shown that the combination of AMB and TAD (middle) relaxed contraction more significantly than the combination of BOS and TAD (bottom).

In FIG. 4, the contraction graphs show the effects of TAD in combination with AMB or BOS on ET-1-induced contraction of rat aortic rings (up: no treatment; middle: AMB+TAD; down: BOS+TAD). Apparently, the combination of AMB and TAD is much more effective than the combination of BOS and TAD.

Figure 5:
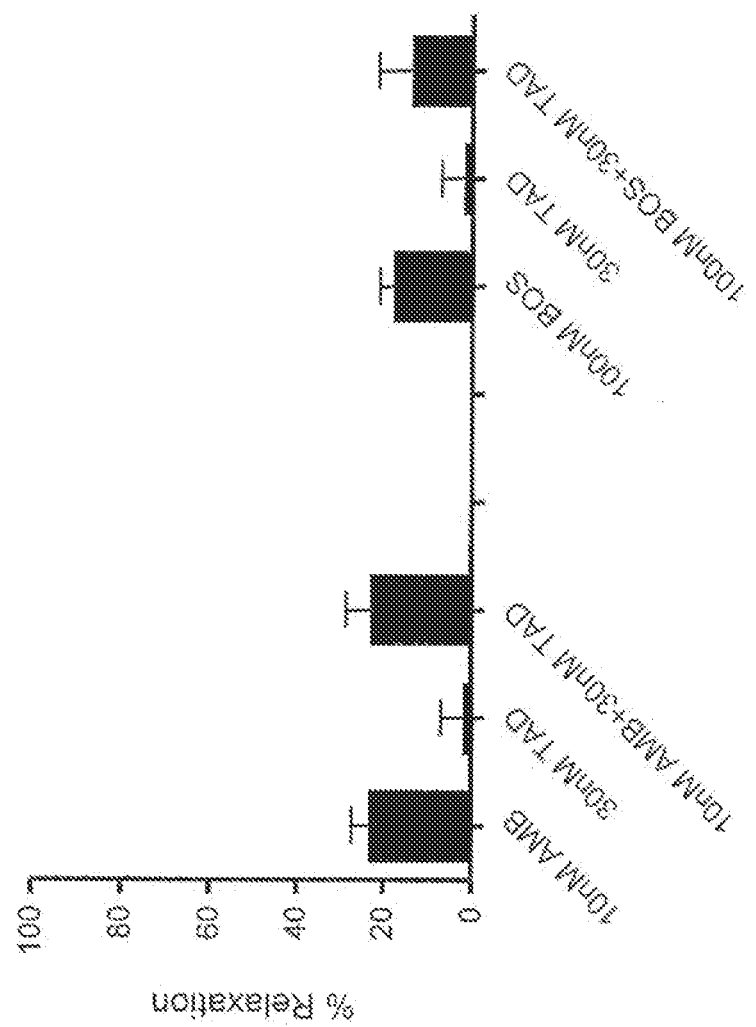
FIG. 5 shows that endothelium involved in co-action or additive effect of ET Receptor antagonists with TAD.

In endothelium-denuded pulmonary arterial rings, 30 nM tadalafil failed to inhibit contraction induced by ET-1 whereas 10 nM ambrisentan reduced contraction by 23±4% (n=4): the drug combination was not more effective than mono-administration of ambrisentan (FIG. 5). FIG. 5 therefore shows that endothelium is involved in additive effect of ET Receptor antagonists with TAD.

Figure 6:
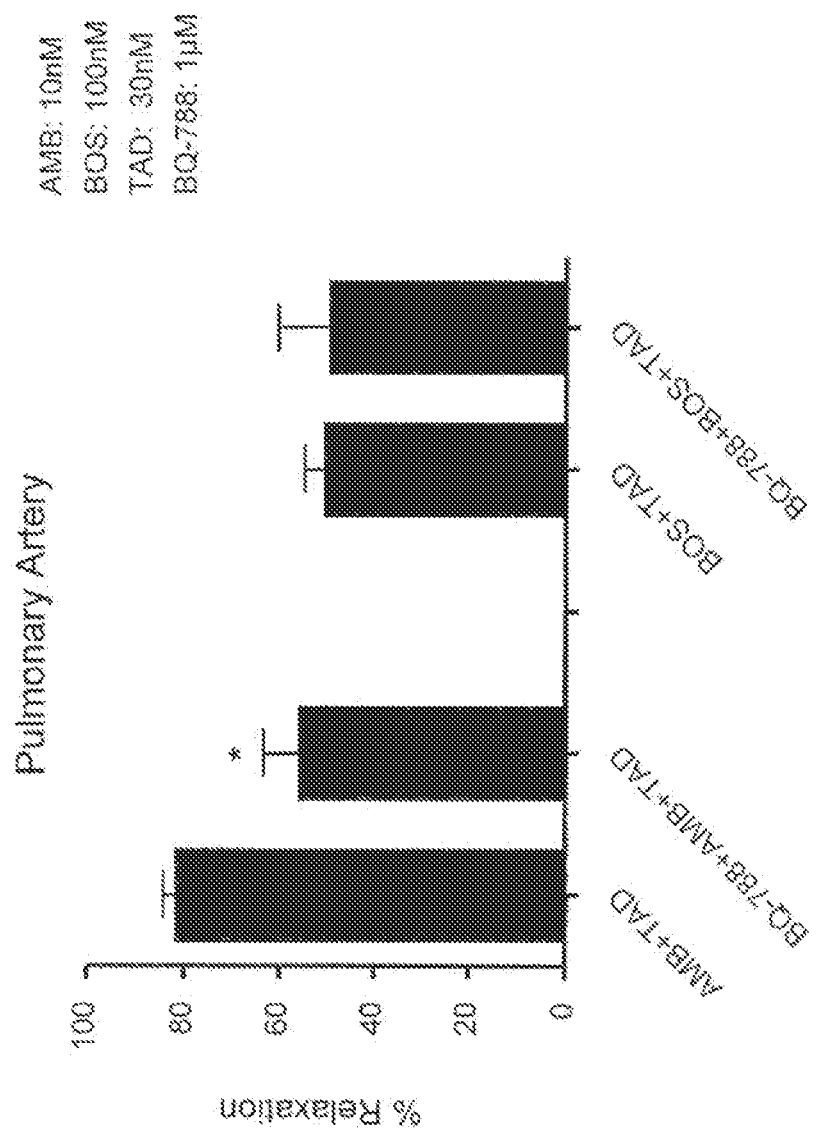
FIG. 6 shows that in the presence of BQ-788, a selective type-B endothelin receptor antagonist, the combination effect of AMB with TAD was significantly reduced. This indicates that ET type-B receptor is involved in co-action effect of AMB with TAD.

In the presence of 1 μM BQ-788, a selective type-B endothelin receptor antagonist, the combination effect of 10 nM ambrisentan with 30 nM tadalafil was significantly reduced from 85±3% (n=4) to 56±7% (FIG. 6, n=4, P<0.05 vs. combination of ambrisentan with tadalafil) which is close to the additive effect of 30 nM tadalafil with 100 nM bosentan or 30 nM macitentan. BQ-788 did not have an effect on the relaxation by combination of tadalafil with bosentan (FIG. 6).

Figure 7:
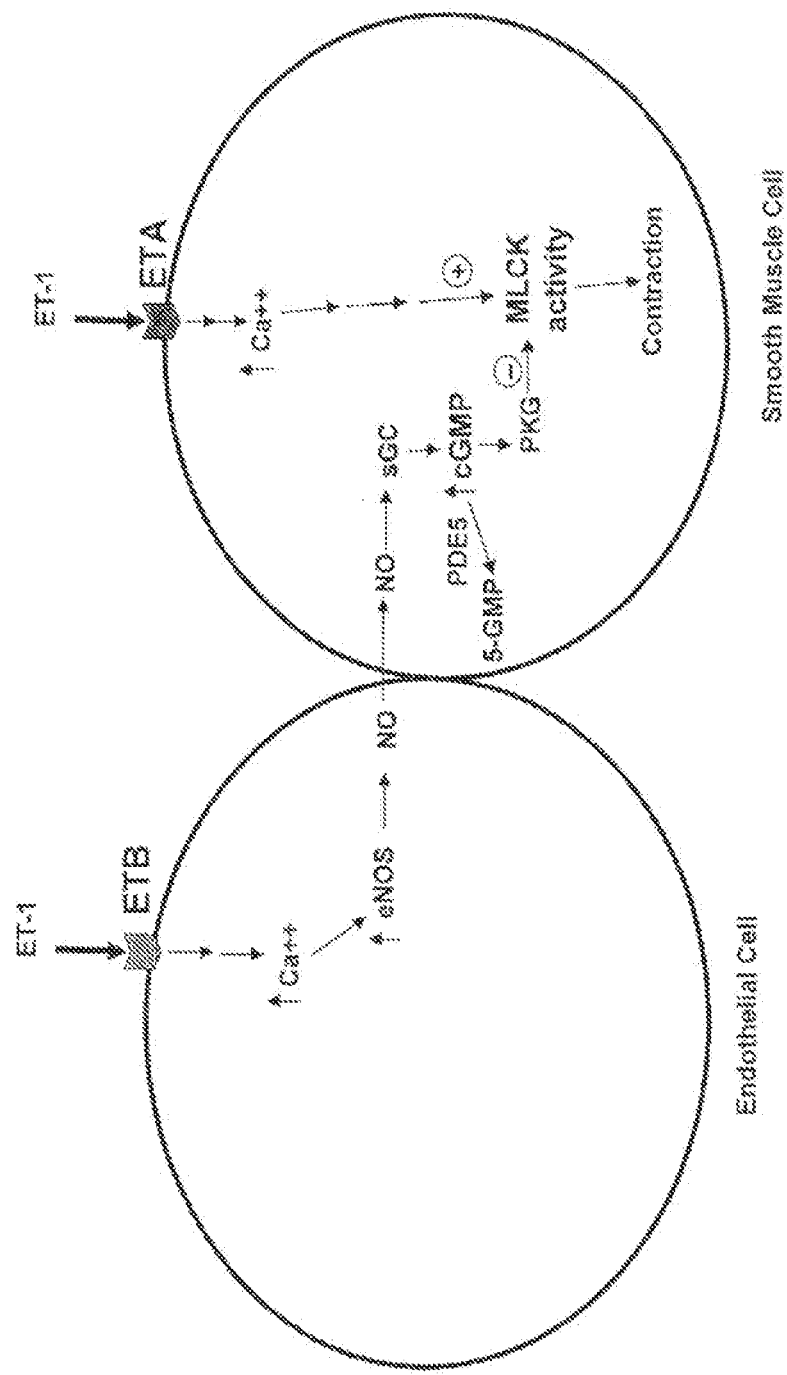
FIG. 7 illustrates the ET-1 and PDE5 signaling in endothelial cells and smooth muscle cells.

These data suggest that the co-action of ambrisentan and tadalafil inhibiting endothelin-induced vasoconstriction and the type-B endothelin receptor in endothelium contributes to their enhanced effect on vasorelaxation. The mechanism is explained and illustrated in FIG. 7-9. FIG. 7 illustrates the ET-1 and PDE5 signaling in endothelial cells and smooth muscle cells. A selective type-A ERA such as AMB and a PDE5 inhibitor such as TAD target vasorelaxation from two different pathways leading to enhanced effectiveness (FIG. 8), whereas a non-selective ERA or a selective type-B ERA and a PDE5 inhibitor would not have such benefits because they target the same pathway (FIG. 9).

Based on this mechanism, therefore, the co-action observed in the present example based on the combination of ambrisentan and tadalafil can be extrapolated to other selective type-A ERA's and PDE5 inhibitors.

Example 3

Selective Type-A ERA and PDE5 Inhibitor Attenuated Hypoxia-induced Pulmonary Arterial Hypertension (PAR)

This Example demonstrates the co-action of ambrisentan and tadalafil in a pulmonary arterial hypertension (PAH) animal model,
Method: Pulmonary Arterial Hypertension (PAH) Animal Model Male SD Rats (225-250 g) were housed in chambers under normoxic (sea level) or hypoxic (10% oxygen) conditions for 3 weeks.

Rats were dosed with vehicle (0.5% hydroxypropyl methylcellulose (HPMC), 0.2% Tween 80, and 0.9% benzyl alcohol in water), AMB or TAD (quaque die) beginning the day they were placed in chambers. Plasma was collected when animals were terminated. Table 1 lists the animals used in this study, along with the treatments they received.

TABLE 1

| Group | N | Manipulation | Treatment | Duration |
|---|---|---|---|---|
| 1 | 8 | Normoxia | Vehicle | 3 wks |
| 2 | 12 | Hypoxia | Vehicle | 3 wks |
| 3 | 12 | Hypoxia | 10 mpk TAD | 3 wks |

TABLE 1-continued

| Group | N | Manipulation | Treatment | Duration |
|---|---|---|---|---|
| 4 | 12 | Hypoxia | 1 mpk AMB | 3 wks |
| 5 | 12 | Hypoxia | 10 mpk AMB | 3 wks |
| 6 | 12 | Hypoxia | 1 mpk AMB + 10 mpk TAD | 3 wks |
| 7 | 12 | Hypoxia | 10 mpk AMB + 10 mpk TAD | 3 wks |

For AMB, 1 mg per kg body weight (mpk) resulted in about 17 nM free or unbounded plasma concentration when administered separately, or about 13 nM free or unbounded plasma concentration when administered along with TAD. The free or unbounded plasma concentration for 10 mpk AMB dosing was about 104 nM in both cases. The free or unbounded plasma concentrations of TAD was about 24 nM when administered separately, or about 26 nM when administered with AMB, whether 1 mpk or 10 mpk.

Figure 10:
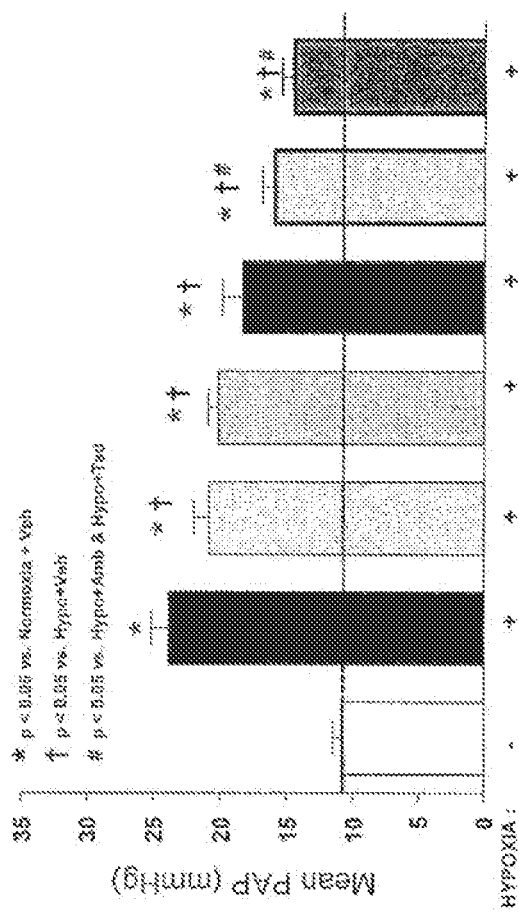
FIG. 10 demonstrates the co-action between TAD with AMB in an in vivo pulmonary arterial hypertension (PAH) animal model.

Results:

Compared to animals treated with the vehicle, treatment with mono-administration of TAD or AMB inhibited hypoxia-induced mean pulmonary arterial pressure (mPAP) (FIG. 10). TAD, 1 mpk AMB and 10 mpk AMB showed 23.2±1.3%, 28.4±1.1% and 42.1±2.4% inhibition of PAP (mPAP±SEM), respectively.

When administered together, TAD and 1 mpk AMB led to a 60.8±3.7% PAP inhibition, which was statistically significantly greater than the additive effect of mono-administration of each agent (51.6±1.8%, $p<0.05$). Likewise, the co-administration of TAD and 10 mpk AMB achieved a 71.7±2.3% PAP inhibition, which was also statistically significantly greater than the additive effect of mono-administration of each agent (65.3±1.9%, $p<0.05$).

Therefore, this example demonstrates, in vivo, the co-action of ambrisentan and tadalafil in inhibiting PAH.

We claim:

1. A method for treating pulmonary arterial hypertension in a human patient in need thereof, comprising co-administering to the patient a therapeutic amount of ambrisentan and a therapeutically effective amount of tadalafil, wherein the weight ratio of the ambrisentan to the tadalafil is about 1:2 or about 1:3.

2. The method of claim 1, wherein the weight ratio of the ambrisentan to the tadalafil is about 1:2.

3. The method of claim 1, wherein the ambrisentan and the tadalafil are administered in a sequential manner.

4. The method of claim 1, wherein the ambrisentan and the tadalafil are administered at the same time.

5. The method of claim 1, wherein the ambrisentan and the tadalafil are administered orally or parenterally.

6. The method of claim 1, wherein the weight ratio of the ambrisentan to the tadalafil is about 1:3.

* * * * *